US006280964B1

(12) United States Patent
Kavanaugh et al.

(10) Patent No.: US 6,280,964 B1
(45) Date of Patent: *Aug. 28, 2001

(54) BINDING SITES FOR PHOSPHOTYROSINE BINDING DOMAINS

(75) Inventors: William Michael Kavanaugh, Mill Valley; Lewis T. Williams, Tiburon, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/423,646

(22) Filed: Apr. 14, 1995

(51) Int. Cl.$^7$ .................................................. G01N 33/53
(52) U.S. Cl. .............................. 435/7.8; 435/15; 435/7.2; 530/300; 530/324; 530/325; 530/326; 530/327; 530/328; 530/329; 530/330; 530/810; 436/501; 436/503; 436/504
(58) Field of Search ............................. 435/69.2, 4, 61, 435/7.8, 7.2, 15; 514/2, 12–17; 530/300, 324, 325, 326, 327, 328, 329, 330, 413, 810; 436/501, 503, 504

(56) References Cited

U.S. PATENT DOCUMENTS

| 5,352,660 | 10/1994 | Pawson .................................... 514/12 |
| 5,744,313 | * 4/1998 | Williams ................................ 435/7.1 |

FOREIGN PATENT DOCUMENTS

| WO 92/13001 | 8/1992 | (WO) . |
| WO 94/07913 | 4/1994 | (WO) . |

OTHER PUBLICATIONS

Wingard et al., Human Pharmacology, Mosby Year Book, pp. 16–17), 1991.*
Damen et al., "Erythropoietin Stimulates the Tyrosine Phosphorylation of Shc and it Association with Grb2 and a 145–Kd Tyrosine Phosphorylated Protein," *Blood*, 83(8):2296–2303 (1993).
Adams et al., "3,400 new expressed sequence tags identify diversity of transcripts in human brain," *Nature*, 4:256–267 (1993).
Akiyama et al., "The Transforming Potential of the c–erbB–2 Protein Is Regulated by Its Autophosphorylation at the Carboxyl–Terminal Domain," *Molecular and Cellular Biology*, 11(2): 833–842 (1991).
Bibbins et al., "Binding of the Src SH2 Domain to Phosphopeptides Is Determined by Residues in both the SH2 Domain and the Phosphopeptides," *Molecular and Cellular Biology*, 13(12):7278–7287 (1993).

Birge et al., "Tyrosine–phosphorylated Epidermal Growth Factor Receptor and Cellular p130 Provide High Affinity Binding Substrates to Analyze Crk–Phosphotyrosine–dependent Interactions In Vitro," *J. Biol. Chem.*, 267(15):10588–10595 (1992).
Blaikie et al., "A Region in Shc Distinct from the SH2 Domain Can Bind Tyrosine–phosphorylated Growth Factor Receptors," *J. Biol. Chem.*, 269(51):32031–32034 (1994).
Campbell et al, "Polyoma middle tumor antigen interacts with SHC protein via the NPTY (Asn–Pro–Thr–Tyr) motif in middle tumor antigen," *Proc. Natl. Acad. Sci. USA*, 91:6344–6348 (1994).
Cantley et al., "Oncogenes and Signal Transduction," *Cell*, 64:281–302 (1991).
Domchek et al., "Inhibition of SH2 Domain/Phosphoprotein Association by a Nonhydrolyzable Phosphonopeptide," *Biochemistry*, 31(41):9865–9870 (1992).
Dougall et al., "The neu–oncogene: signal transduction pathways, transformation mechanisms and evolving therapies," *Oncogene*, 9:2109–2123 (1994).
Egan et al., "Association of Sos Ras exchange protein with Grb2 is implicated in tyrosine kinase signal transduction and transformation," *Nature*, 363:45–51 (1993).
Escobedo et al., "A Phosphatidylinositol–3 Kinase Binds to Platelet–Derived Growth Factor Receptors through a Specific Receptor Sequence Containing Phosphotyrosine," *Molecular and Cellular Biology*, 11(2):1125–1132 (1991).
Gustafson et al., "Phosphotyrosine–Dependent Interaction of SHC and Insulin Receptor Substrate 1 with the NPEY Motif of the Insulin Receptor via a Novel Non–SH2 Domain," *Molecular and Cellular Biology*, 15(5):2500–2508 (1995).
Hazan et al., Identification of Autophosphorylation Sites of HER2/neu, *Cell Growth & Differentiation*, 1:3–7 (1990).
Katzav, Shulamit, "Single point mutations in the SH2 domain impair the transforming potential of vav and fail to activate proto–vav," *Oncogene*, 8:1757–1763 (1993).
Kavanaugh et al., "Modification of the 85–Kilodalton Subunit of Phosphatidylinositol–3 Kinase in Platelet–Derived Growth Factor–Stimulated Cells," *Molecular and Cellular Biology*, 12(8):3415–3424 (1992).

(List continued on next page.)

*Primary Examiner*—Lorraine Spector
*Assistant Examiner*—Eliane Lazar-Wesley
(74) *Attorney, Agent, or Firm*—Townsend and Townsend and Crew LLP

(57) ABSTRACT

The present invention generally provides peptides that comprise a recognition sequence motif for phosphotyrosine binding proteins. In particular, the present invention provides peptides which comprise a core sequence of amino acids, and analogs thereof, which are recognized and bound by the PTB (phosphotyrosine binding) domain. Also provided are methods of using the peptides of the invention in diagnostic, screening and therapeutic applications.

19 Claims, 3 Drawing Sheets

OTHER PUBLICATIONS

Kavanaugh et al., "An Alternative to SH2 Domains for Binding Tyrosine–Phosphorylated Proteins," *Science*, 266:1862–1865 (1994).

Marengere et al., "Identification of Residues in GTPase–activating Protein Src Homology 2 Domains That Control Binding to Tyrosine Phosphorylated Growth Factor Receptors and p62," *J. Biol. Chem.*, 267(32):22779–22786 (1992).

Mayer et al., "Point Mutations in the abl SH2 Domain Coordinately Impair Phosphotyrosine Binding In Vitro and Transforming Activity In Vivo," *Molecular and Cellular Biology*, 12(2):609–618 (1992).

Obermeier et al., "Identification of Trk Binding Sites for SHC and Phosphatidylinositol 3'–Kinase and Formation of a Multimeric Signaling Complex," *J. Biol. Chem.*, 268(31):22963–22966 (1993).

Okabayashi et al., "Tyrosines 1148 and 1173 of Activated Human Epidermal Growth Factor Receptors Are Binding Sites of Shc in Intact Cells," *J. Biol. Chem.*, 269(28):18674–18678 (1994).

Pawson et al., "SH2 and SH3 Domains: From Structure to Function," *Cell*, 71:359–362 (1992).

Pelicci et al., "A Novel Transforming Protein (SHC) with an SH2 Domain Is Implicated in Mitogenic Signal Transduction," *Cell*, 70:93–104 (1992).

Prigent et al., "Identification of c–erbB–3 binding sites for phosphatidylinositol 3'–kinase and SHC using an EGF receptor/c–erbB–3 chimera," *EMBO Journal*, 13(12):2831–2841 (1994).

Rozakis–Adcock et al., "Association of the Shc and Grb2/Sem5 SH2–containing proteins is implicated in activation of the Ras pathway by tyrosine kinases," *Nature*, 360:689–692 (1992).

Sadowski et al., "A Noncatalytic Domain Conserved among Cytoplasmic Protein–Tyrosine Kinases Modifies the Kinase Function and Transforming Activity of Fujinami Sarcoma Virus P130$^{gag-fps}$, " *Molecular and Cellular Biology*, 6(12):4396–4408 (1986).

Segatto et al., "The Role of Autophosphorylation in Modulation of erbB–2 Transforming Function," *The new Biologist*, 2(2):187–195 (1990).

Segatto et al., "Shc products are substrates of erbB–2 kinase," *Oncogene*, 8:2105–2112 (1993).

Songyang et al., "SH2 Domains Recognize Specific Phosphopeptide Sequences," *Cell*, 72:767–778 (1993).

Waksman et al., "Binding of a High Affinity Phosphotyrosyl Peptide to the Src SH2 Domain: Crystal Structures of the Complexed and Peptide–free Forms," *Cell*, 72:779–790 (1993).

* cited by examiner

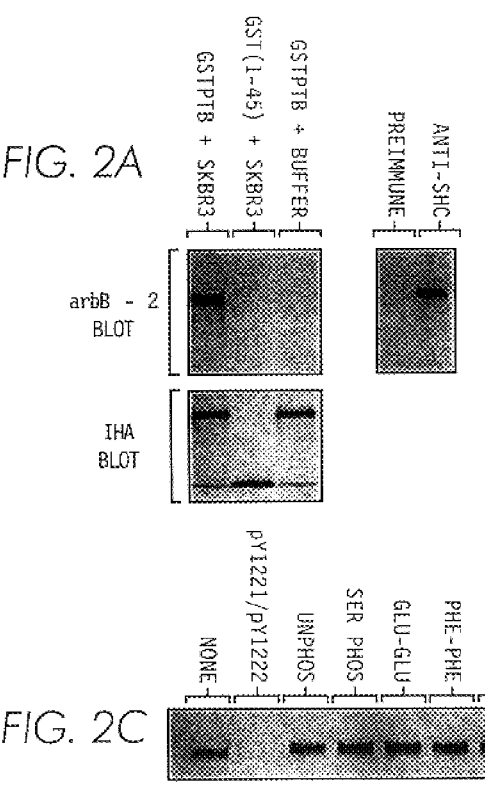
FIG. 2A
FIG. 2C
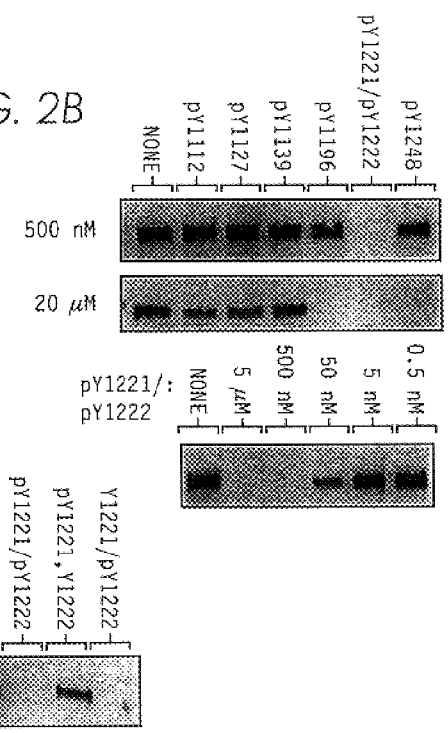
FIG. 2B

BINDING SITES FOR PHOSPHOTYROSINE BINDING DOMAINS

This invention was made with Government support under Grant Nos. K11HL02410 and R01-HL32898, awarded by the National Institutes of Health. The Government has certain rights in this invention.

BACKGROUND OF THE INVENTION

The present invention generally provides peptides that comprise a recognition sequence motif for phosphotyrosine binding proteins. In particular, the present invention provides peptides which comprise a core sequence of amino acids, and analogs thereof, which are recognized and bound by the PTB phosphotyrosine binding domain. Also provided are methods of using the peptides of the invention in diagnostic, screening and therapeutic applications.

Receptor signaling pathways are the subject of widespread research efforts. A better understanding of these signaling pathways will lead to the design of new and more effective drugs in the treatment of many diseases. Of particular interest are the growth factor and related receptor signaling pathways and their role in cell growth and differentiation. Binding of a particular growth factor to its receptor on the cell plasma membrane can stimulate a wide variety of biochemical responses, including changes in ion fluxes, activation of various kinases, alteration of cell shape, transcription of various genes and modulation of enzymatic activities in cellular metabolism.

In particular, upon binding an external ligand, a receptor may undergo auto-phosphorylation of specific tyrosine residues, and/or may phosphorylate other proteins. This tyrosine phosphorylation creates binding sites for cytoplasmic signaling proteins which have specific domains that recognize the phosphorylated tyrosine and adjacent residues. Once bound, these signaling proteins may in turn be activated. The activated signaling proteins then may effect downstream processes. Pawson and Gish, *Cell* 71:359–362 (1992).

Src Homologous, or "SH2" domains are amino acid sequences that are similar to a 100-residue, non-catalytic region of the Src tyrosine kinase and are present in various signaling molecules. Sadowski et al., *Mol. Cell. Biol.* 6, 4396 (1986). SH2 domains are functional protein motifs that bind tyrosine-phosphorylated targets by recognizing phosphotyrosine and specific adjacent residues. J. A. Escobedo et al., *Mol. Cell. Biol.* 11, 1125 (1991); L. C. Cantley et al. *Cell* 64, 281 (1991); T. Pawson and G. D. Gish *Cell* 71, 359 (1992); S. Zhou et al. *Cell* 72, 767 (1993); G. Waksman, S. E. Shoelson, N. Pant, D. Cowburn, J. Kuriyan *Cell* 72, 779 (1993). Activation of tyrosine kinases by growth factors, cytokines, and oncogenic agents therefore serves as a switch for assembling SH2 domain-containing proteins with their tyrosine-phosphorylated targets in signaling complexes, in which downstream effectors are activated.

The use of phosphotyrosine binding domains, including SH2 domains, has been discussed in methods for identifying targets of tyrosine kinases in cells, and thus identifying intermediates in cell signaling pathways. See, PCT Patent Application No. WO 92/13001, to Schlessinger et al.

The specific use of SH2 domains and subdomains in affecting the SH2/phosphorylated ligand regulatory scheme, or screening for compounds which affect SH2 binding in this regulatory scheme, has been previously described. See, U.S. Pat. No. 5,352,660 to A. J. Pawson. The use of these domains in assaying for the presence of SH2 binding phosphoproteins has also been described.

Specific SH2 containing proteins include the products of the SHC gene. The SHC (which stands for SH2, Collagen) gene encodes a transforming protein, expressed as 46- and 52-kD proteins that are tyrosine phosphorylated in response to a number of growth factors, e.g., PDGF, EGF and FGF, and have been implicated as mediators of signaling from growth factor receptor and non-receptor tyrosine kinases to Ras. G. Pelicci et al. *Cell* 70, 93–104 (1992); M. Rozakis-Adcock et al. *Nature,* 360:689 (1992).

Thus, a great deal of attention has been directed toward studying these SH2 domains and their role in cell signaling pathways. However, SH2 domains, and the proteins which comprise them, are not the only phosphotyrosine binding mediators of such pathways.

A new phosphotyrosine binding ("PTB") domain has been identified within the sequence of the SHC protein. See, Kavanaugh and Williams, *Science (*1994) 266:1862–1865. This PTB domain was reported to specifically bind the tyrosine phosphorylated version of a target protein, which target protein was phosphorylated upon cell activation/stimulation, e.g., anti-IgM stimulated B cells, IL-6 stimulated HepG2 hepatoma cells, LIF stimulated CCE embryonic stem cells. The amino acid sequence of this domain is unlike that of any member of the known SH2 domain family. Therefore, although the nature of phosphotyrosine binding by the PTB domain is similar to that of the SH2 domain, functionally, and mechanistically, the two are very different.

The study of these cell signaling pathways, and the ability to control them requires identification and characterization of proteins which contain phosphotyrosine binding domains and the protein sequences to which they bind. The present invention meets these and other needs.

SUMMARY OF THE INVENTION

The present invention generally provides substantially pure peptides which are capable of binding a PTB domain, wherein the peptide is from 5 to 100 amino acids in length, and comprises a core sequence of amino acids $NX_3X_1X_2X_4$; where $X_1$ is selected from the group consisting of Y, pY or an analog thereof, E, T, D, Q, A and F; $X_2$ is selected from pY or an analog thereof, and Y, provided that at least one of $X_1$ and $X_2$ is pY, or an analog thereof; $X_3$ is selected from the group consisting of L and A; and $X_4$ is selected from the group consisting of W, L, S, F and Q (SEQ ID NO:1). In a preferred embodiment, at least one of $X_1$ and $X_2$ will be an analog of phosphotyrosine, and said analog is (phosphonomethyl)-phenylalanine. In preferred aspects, the peptides are from 6 to 100 amino acids in length, and comprise a core sequence of amino acids $X_5NX_3X_1X_2X_4$, wherein $X_5$ is selected from the group consisting of D, S, E and A (SEQ ID NO:2). In still more preferred peptides, $X_2$ will be pY. In particularly preferred embodiments, the peptides will be from 6 to 100 amino acids in length, and comprise a core sequence of amino acids selected from the group consisting of $DNX_3X_1pYX_4$ (SEQ ID NO:3) and $ENX_3X_1pYX_4$ (SEQ ID NO:4), where $X_4$ is selected from the group consisting of W and F.

Especially preferred peptides will be from 12 to 100 amino acids in length, and which comprise a core sequence of amino acids selected from the group consisting of: AFDNLY(pY)WDQNS (SEQ ID NO:5); AFDNL(pY)YWDQNS (SEQ ID NO:6); and AFDNL(pY)(pY)WDQNS (SEQ ID NO:7). As preferred, are peptides which are from 21 to 100 amino acids in length and which comprise a core sequence of amino acids selected from the group consisting of:

PAFSPAFDNLY(pY)WDQNSSEQG (SEQ ID NO:8); PAFSPAFDNL(pY)YWDQNSSEQG (SEQ ID NO:9); PAFSPAFDNL(pY)(pY)WDQNSSEQG (SEQ ID NO:10); PAFSPAADNLY(pY)WDQNSSEQG (SEQ ID NO:11); PAFSPAADNL(pY)YWDQNSSEQG (SEQ ID NO:12); PAFSPAADNL(pY) (pY)WDQNSSEQG (SEQ ID NO:13); PAFSPAFANLY(pY)WDQNSSEQG (SEQ ID NO:14); PAFSPAFANL(pY)YWDQNSSEQG (SEQ ID NO:15); PAFSPAFANL(pY)(pY)WDQNSSEQG (SEQ ID NO:16); PAFSPAFSNLY(pY)WDQNSSEQG (SEQ ID NO:17); PAFSPAFSNL(pY)YWDQNSSEQG (SEQ ID NO:18); PAFSPAFSNL(pY)(pY)WDQNSSEQG (SEQ ID NO:19); PAFSPAFDNAY(pY)WDQNSSEQG (SEQ ID NO:20); PAFSPAFDNA(pY)YWDQNSSEQG (SEQ ID NO:21); PAFSPAFDNA(pY)(pY)WDQNSSEQG (SEQ ID NO:22); PAFSPAFDNLA(pY)WDQNSSEQG (SEQ ID NO:23); PAFSPAFDNLF(pY)WDQNSSEQG (SEQ ID NO:24); PAFSPAFDNLY(pY)FDQNSSEQG (SEQ ID NO:25); PAFSPAFDNL(pY)YFDQNSSEQG (SEQ ID NO:26); PAFSPAFDNL(pY)(pY)FDQNSSEQG (SEQ ID NO:27); PAFSPAFDNLY(pY)WAQNSSEQG (SEQ ID NO:28); PAFSPAFDNL(pY)YWAQNSSEQG (SEQ ID NO:29); PAFSPAFDNL(pY)(pY)WAQNSSEQG (SEQ ID NO:30); PAFSPAFDNLY(pY)WDANSSEQG (SEQ ID NO:31); PAFSPAFDNL(pY)YWDANSSEQG (SEQ ID NO:32); PAFSPAFDNL(pY)(pY)WDANSSEQG (SEQ ID NO:33); PAFSPAFDNLY(pY)WDNNSSEQG (SEQ ID NO:34); PAFSPAFDNL(pY)YWDNNSSEQG (SEQ ID NO:35); PAFSPAFDNL(pY)(pY)WDNNSSEQG (SEQ ID NO:36); PAFSPAFDNLY(pY)WDDNSSEQG (SEQ ID NO:37); PAFSPAFDNL(pY)YWDDNSSEQG (SEQ ID NO:38); PAFSPAFDNL(pY)(pY)WDDNSSEQG (SEQ ID NO:39); PAFSPAFDNLY(pY)WDQASSEQG (SEQ ID NO:40); PAFSPAFDNL(pY)YWDQASSEQG (SEQ ID NO:41); PAFSPAFDNL(pY)(pY)WDQASSEQG (SEQ ID NO:42); PAFSPAFDNLY(pY)WDQNASEQG (SEQ ID NO:43); PAFSPAFDNL(pY)YWDQNASEQG (SEQ ID NO:44); and PAFSPAFDNL(pY)(pY)WDQNASEQG (SEQ ID NO:45).

In an alternate embodiment, the present invention provides substantially pure peptides which are capable of binding a PTB domain, wherein the peptides are from 21 to about 100 amino acids in length and which comprise a core sequence of amino acids selected from the group consisting of AFGGAVENPE(pY)LAPRAGTASQ (SEQ ID NO:46) and EGTPTAENPE(pY)LGLDVPV (SEQ ID NO:47).

In a further embodiment, the present invention provides compositions which comprise the peptides of the present invention and pharmaceutically acceptable carriers.

In another embodiment, the present invention provides a method of determining whether a protein comprises a PTB domain. The method comprises the steps of contacting the protein with a peptide of the present invention, and determining whether the peptide binds to the protein. The binding of the peptide to the protein is indicative that the protein comprises a PTB domain. In preferred aspects, the protein is attached to a solid support prior to contacting the protein with the peptide of the present invention, and the peptide used in the contacting step further comprises a detectable group fused to the peptide. The determining step then comprises assaying for the presence of the detectable group. Alternatively, the peptide of the invention will be attached to a solid support prior to contacting the protein with the peptide of the invention.

In an additional embodiment, the present invention provides a method of determining whether a test compound is an agonist or antagonist of a PTB domain/phosphorylated ligand interaction. The method comprises the steps of incubating the test compound with a protein comprising a PTB domain, and a peptide of the invention, determining the amount of protein bound to the peptide during the incubating step, and comparing the amount of protein bound to the peptide during the incubating step to an amount of protein bound to the peptide in the absence of the test compound. The increase or decrease in the amount of protein bound to the peptide in the presence of the test compound will be indicative that the test compound is an agonist or antagonist of PTB domain/phosphorylated ligand interaction, respectively.

In yet another embodiment of the present invention is provided a method of inhibiting the binding of a PTB domain-containing protein to a tyrosine phosphorylated target, comprising contacting the PTB domain-containing protein with an effective amount of the peptide of the invention. In a preferred aspect, the tyrosine phosphorylated target is c-erbB2. In another preferred aspect, the PTB domain-containing protein is SHC.

Also provided by the present invention, is a method of obtaining substantially pure PTB domain-containing protein from a mixture of different proteins. The method comprises the steps of providing a peptide of the present invention bound to a solid support. The mixture of different proteins is contacted with the peptide bound to the solid support whereby the PTB domain-containing protein is bound to the peptide. The solid support is washed to remove unbound proteins, and substantially pure PTB domain-containing protein is then eluted from the solid support.

In an additional embodiment, the present invention provides a method of treating a patient suffering from a proliferative cell disorder. The method comprises administering to the patient an effective amount of the peptide of the present invention. Typically, the proliferative cell disorder is selected from the group consisting of atherosclerosis, inflammatory joint disease, psoriasis, restinosis and cancer. Preferably, the proliferative cell disorder is cancer, and more preferably, breast cancer.

BRIEF DESCRIPTION OF THE DRAWINGS

FIGS. 2A–C shows the association of c-erbB2 with the PTB domain. Panel A shows GST-PTB and GST-(1–45) (residues 1– 45 of SHC, containing no PTB domain) fusion proteins, tagged with the influenza hemagglutinin (IHA) epitope, and incubated with lysate of SKBR3 cells (containing c-erbB2) or with buffer. Anti-IHA immunoprecipitates of each were separately blotted with anti-c-erbB2 ("erbB-2 blot") and anti-IHA 12CA5 antibodies ("IHA blot"). Also shown are blots of immunoprecipitates using preimmune serum and anti-SHC serum. Panel B shows a blot of IHA tagged GST-PTB, incubated with SKBR3 lysate in the presence or absence of the indicated peptides derived from c-erbB2 (upper blot), and with varied concentrations of the peptide PAFSPAFDNL(pY)(pY)WDQNSSEQG ("pY1221/pY1222") (lower blot). Panel C shows a blot of IHA tagged GST-PTB, incubated with SKBR3 lysate in the presence of 500 nM of the indicated pY substituted peptides.

DESCRIPTION OF THE PREFERRED EMBODIMENT

Figure 1:
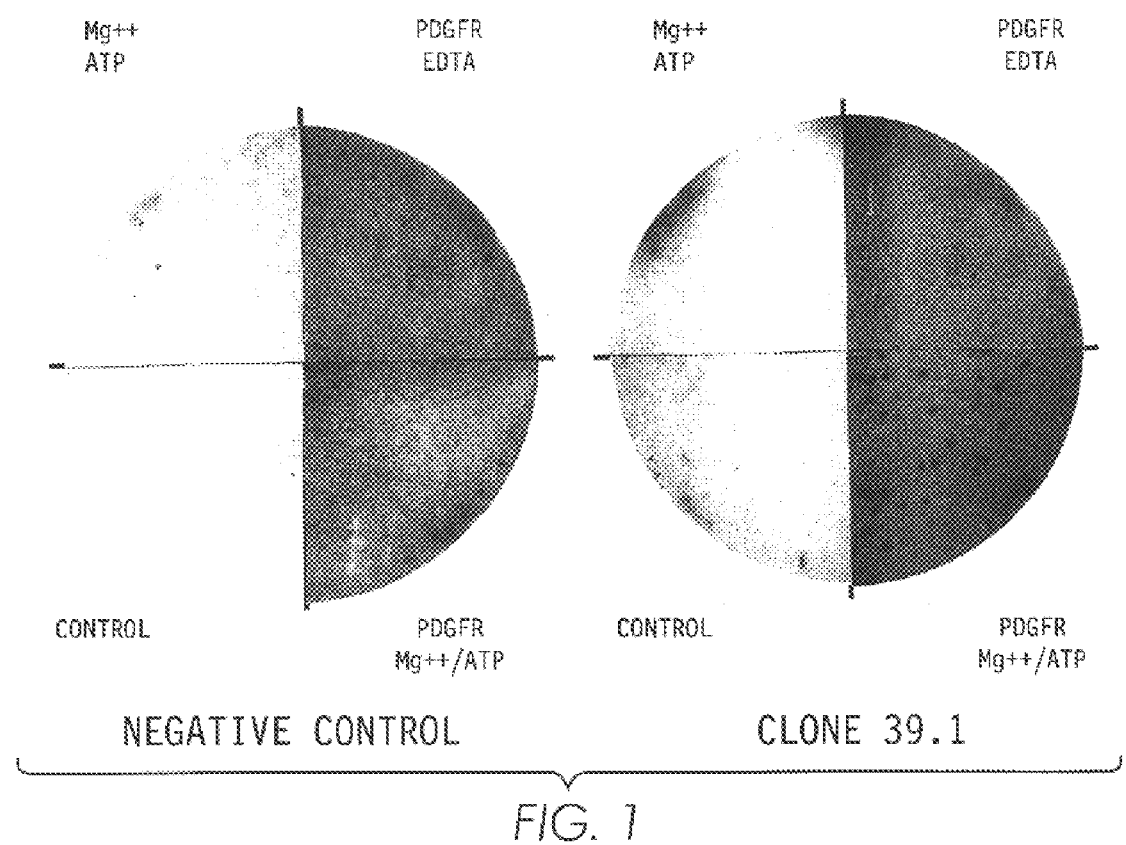
FIG. 1 shows proteins expressed from a λ gt11 cDNA library, immobilized on filters, phosphorylated in vitro using recombinant PDGF receptor kinase, followed by hybridization with $^{32}$P-labeled PTB domain. Shown is a positive (clone 39.1) and representative negative plaque purified by successive rounds of screening, then transferred to a filter. Quadrants of the filter were treated as indicated prior to hybridization with $^{32}$P-labeled PTB domain.

The present invention generally provides peptides which comprise a sequence motif which is recognized and bound by phosphotyrosine binding proteins. More particularly, the peptides of the present invention are recognized and bound by proteins which comprise a PTB domain.

These peptides, or their analogs, may generally be used in blocking or inhibiting PTB domain/phosphorylated ligand interactions, both in vitro and in vivo. As a result, the peptides of the present invention can be useful as antagonists of PTB domain/phosphorylated ligand interaction, for controlling or inhibiting cell signalling pathways which rely on these PTB domain/phosphorylated ligand interactions, i.e., growth factor dependent activation or stimulation of cells, and growth factor initiated mitogenesis. The peptides of the present invention can also be useful as affinity ligands or probes, in the identification, purification, and/or characterization of PTB domain containing proteins, or, alternatively, as target peptides in screening for agonists or antagonists of PTB domain/phosphorylated ligand interaction.

I. Definitions

As used herein, the twenty conventional, or natural amino acids and their abbreviations follow conventional usage (*Immunology—A Synthesis*, 2nd Edition, E. S. Golub and D. R. Gren, Eds., Sinauer Associates, Sunderland, Mass. (1991)). Specifically, abbreviations for the amino acid residues as used herein are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; Y, Tyr. Phosphotyrosine is denoted by pY, and (phosphonomethyl) phenylalanine is denoted by Pmp.

Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional or unnatural amino acids include amino acids well known in the art, but which are not included in the twenty conventional amino acids, such as: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

The term "analog" as used herein refers to compounds which are generally structurally similar to the compound of which they are an analog, or "parent" compound. Generally analogs will retain certain characteristics of the parent compound, e.g., biological or pharmacological activity, while lacking other, less desirable characteristics, e.g., antigenicity, proteolytic instability, toxicity, and the like. As applied to polypeptides, the term "analog" generally refers to polypeptides which are comprised of a segment of about at least 3 amino acids that has substantial identity to at least a portion of a PTB domain-binding peptide, and which has at least one of the following properties: (1) specifically binds to the PTB domain, and (2) affects or blocks a PTB domain-containing protein mediated phenotype. Typically, analog peptides comprise a conservative amino acid substitution (or addition or deletion) with respect to the naturally-occurring sequence. Analogs typically are at least 5 amino acids long, preferably at least 20 amino acids long or longer, most usually being as long as a minimal length binding/recognition sequence identified by methods for identifying PTB domain-binding peptides. Some analogs may lack substantial biological activity but may still be employed for various uses, such as for raising antibodies to predetermined epitopes, as an immunological reagent to detect and/or purify reactive antibodies by affinity chromatography, or as a competitive or noncompetitive agonist, antagonist, or partial agonist of PTB domain function.

As used herein, the term "peptide" and "polypeptide" refer to macromolecules which comprise a multiplicity of amino or imino acids (or their equivalents) in peptide linkage, wherein said peptides may comprise or lack post-translational modifications (e.g., glycosylation, cleavage, phosphorylation, side-chain derivation, and the like).

As used herein, the terms "label" or "labeled" refer to incorporation of a detectable marker, e.g., by incorporation of a radiolabeled amino acid or attachment of biotinyl moieties to a polypeptide, wherein the attached biotinyl moieties can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I) fluorescent labels (e.g., FITC, rhodamine, lanthanide phosphors), enzymatic labels (e.g., horseradish peroxidase, (β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means that the particular peptide is the predominant species present (i.e., on a weight/volume percentage, it is the most abundant single species within the composition), and preferably a substantially purified fraction is a composition wherein the peptide comprises at least about 50 percent (w/v) of all macromolecular species present. Generally, a substantially pure composition will comprise more than about 80 to 90 percent of all protein present in the composition. Most preferably, the peptide is purified to essential homogeneity (contaminant proteins cannot be detected in the composition by conventional detection methods) wherein the composition consists essentially of a single protein species.

II. Identification of Peptides

The PTB domain was originally identified as a 186-residue segment of the signaling protein SHC which binds specifically to the tyrosine-phosphorylated form of an unidentified 145 kDa protein in response to many growth factors, but which is structurally dissimilar to members of the SH2 domain family. See, Kavanaugh and Williams, *Science* (1994) 266:1862–1865.

To determine the targets to which PTB domains bind, a method of screening a library of tyrosine phosphorylated proteins was developed. Standard expression cloning systems are generally unsuitable, because they do not permit screening for phosphorylation-dependent protein-protein interactions. An expression cloning approach which allowed identification of proteins which bound PTB domain only when tyrosine-phosphorylated, was developed. Standard methods were used to express proteins from a λ gt11 cDNA library and immobilize them on filters. See, e.g., Sambrook, et al., Molecular Cloning: A Laboratory Manual (Cold Spring Harbor Laboratory Press, 2nd ed. 1989). The proteins on filters were then phosphorylated in vitro with recombinant tyrosine kinases, washed, incubated with $^{32}$P-labeled PTB domain protein derived from SHC as a probe, and autoradiography was performed. A clone was identified which bound the PTB domain probe only when subjected to phosphorylation conditions prior to hybridization (FIG. 1).

The positive clone was identified as corresponding to amino acids 1086 to 1255 of c-erbB2/c-neu/HER2 protein, a tyrosine kinase receptor proto-oncogene (See FIG. 1). This region of c-erbB2 contains seven tyrosines, five of which have been shown to be autophosphorylation sites. Hazan, et al., *Cell Growth Differ* (1990) 1:3–7, Segatto, et al., *New Biol.* (1990) 2:187–195, Akiyama, et al., *Mol. Cell. Biol.* (1991) 11:833–842.

To verify that the PTB domain binds to c-erbB2 which had been autophosphorylated in vivo, PTB domain was incubated with lysate from SKBR3 human breast carcinoma cells, which contain overexpressed and autophosphorylated c-erbB2. C-erbB2 from these cells specifically associated with GST-PTB domain fusion protein, but not with GST fusion protein containing SHC residues 1–45, which lie outside of the PTB domain (FIG. 2A, left panel, see also, Kavanaugh and Williams, *Science* (1994) 266:1862–1865). Further, dephosphorylation of the c-erbB2 from SKBR3 cells with tyrosine-specific phosphatases completely eliminated binding to the PTB domain. Taken together, these data demonstrate that the PTB domain specifically associates with the tyrosine-phosphorylated form of c-erbB2. C-erbB2 associates with SHC in vivo (FIG. 2A, right panel) through a mechanism which requires c-erbB2 autophosphorylation at these sites. Segatto, et al., *Oncogene* (1993) 8:2105–2112. Therefore, c-erbB2 is also an apparent target of the PTB domain in vivo.

Peptides derived from the c-erbB2 sequence were synthesized, substituting phosphotyrosine for each of the seven tyrosines in the c-erbB2 sequence. These peptides were tested for their ability to compete with c-erbB2 from SKBR3 lysate for binding to PTB domain. The peptides tested and their respective IC$_{50}$ values, are listed in Table 1. The IC$_{50}$ is the concentration of peptide required to inhibit 50% of normal binding of PTB to c-erbB2.

TABLE 1

| Peptide Sequence | | Apparent Inhibition (IC$_{50}$) |
|---|---|---|
| PAFSPAFDNL(pY)(pY)WDQNSSEQG ("pY1221/pY1222") | (SEQ ID NO:10) | 50 nM |
| AFDNLY(pY)WDQNS ("Y1221/pY1222") | (SEQ ID NO:5) | 30 nM |
| AFGGAVENPE(pY)LAPRAGTASQ (("pY1196") | (SEQ ID NO:46) | 1 μM |
| EGTPTAENPE(pY)LGLDVPV ("pY1248") | (SEQ ID NO:47) | 1 μM |
| APLACSPQPE(pY)VNQPEVRPQS ("pY1139") | (SEQ ID NO:49) | >100 μM |
| SPHDLSPLQR(pY)SEDPTLPL ("pY1112") | (SEQ ID NO:50) | >100 μM |
| TLPLPPETDG(pY)VAPLACSPQ (pY1127") | (SEQ ID NO:51) | >100 μM |

The peptides PAFSPAFDNL(pY)(pY)WDQNSSEQG (SEQ ID NO:10), AFDNLY(pY)WDQNS, AFGGAVENPE(pY)LAPRAGTASQ and EGTPTAENPE(pY)LGLDVPV (SEQ ID NO:47) showed relatively strong inhibition of PTB domain/c-erbB2 binding with approximate IC$_{50}$s of 50 nM, 30 nM, 1 μM and 1 μM, respectively. The phosphopeptides SPHDLSPLQR(pY)SEDPTPL (SEQ ID NO:50), APLACSPQPE(pY)VNQPEVRPQS (SEQ ID NO:49) and TLPLPPETDG(pY)VAPLACSPQ (SEQ ID NO:51), on the other hand appeared to be ineffective.

Comparison of the sequences of the c-erbB2 derived peptides which were able to bind PTB indicated a common sequence motif of NXX(pY) (SEQ ID NO:52). Furthermore, a similar sequence motif is also found in a number of other signalling proteins associated with cell proliferation, including polyomavirus middle T antigen, the principal transforming protein of the polyomavirus (Campbell, et al., *Proc. Nat'l Acad. Sci. U.S.A.* (1994) 91:6344–6348); Trk tyrosine kinase, associated with signal transduction from nerve growth factors (Obermeier, et al., *J. Biol. Chem.* (1993) 268(31):22963–22966); the EGF receptor (Okabayashi, et al., *J. Biol. Chem.* (1994) 269(28):18674–18678); erbB3, a member of the Type-I (EGF receptor related) family of growth factor receptors (Prigent and Gullick, *EMBO J.* (1994) 13(12):2831–2841); mouse CD3 epsilon chain, integrins and the insulin and IGF receptors. A number of these proteins have been reported to associate with the SHC protein, and the specific sequence motifs are shown in Table 2, below.

TABLE 2

| Protein | Peptide Sequence | |
|---|---|---|
| Middle T Ag. | LLSNPT(pY)SVMR | (SEQ ID NO:53) |
| erbB3 | AFDNPD(pY)WHSRLF | (SEQ ID NO:54) |
| Trk | IENPQ(pY)FSDA | (SEQ ID NO:55) |
| EGF Receptor | SLDNPD(pY)QQDFF | (SEQ ID NO:56) |

From the above data, a common PTB recognition sequence, NXXpY (SEQ ID NO:52) is indicated, and more particularly, the motifs NPXpY (SEQ ID NO:57) and NLXpY (SEQ ID NO:58). These sequence motifs appear to be conserved in a variety of signalling proteins, and are present in the peptides which show the greatest affinity for the PTB domain.

To further characterize the nature of PTB domain binding, peptides were prepared based upon the lead peptide derived from the c-erbB2 protein, PAFSPAFDNL(pY)(pY)WDQNSSEQG ("pY1221/pY1222") (SEQ ID NO:10). These peptides were then tested for their ability to block PTB domain/c-erbB2 binding. The peptides and binding results are shown in Table 3, below.

TABLE 3

| Peptide | | Affinity (IC$_{50}$) |
|---|---|---|
| PAFSPAFDNLYYWDQNSSEQG ("unphos") | (SEQ ID NO:48) | >30 µM |
| PAFSPAFDNL(pS)(pS)WDQNSSEQG ("ser phos") | (SEQ ID NO:69) | >30 µM |
| PAFSPAFDNLEEWDQNSSEQG ("glu-glu") | (SEQ ID NO:70) | >30 µM |
| PAFSPAFDNLFFWDQNSSEQG ("phe-phe") | (SEQ ID NO:71) | >30 µM |
| AFDNL(pY)(pY)WDQNS ("pY1221/pY1222 short") | (SEQ ID NO:7) | 30 nM |
| AFDNL(pY)YWDQNS ("pY1221/Y1222") | (SEQ ID NO:6) | 1 µM |
| AFDNLY(pY)WDQNS ("Y1221/pY1222") | (SEQ ID NO:5) | 30 nM |
| DSWDQNQLFS(pY)(pY)SFAPEGPAN (scrambled 1) | (SEQ ID NO:59) | >30 µM |
| DSW(pY)SQNQLFDSFAPEG(pY)PAN (scrambled 2) | (SEQ ID NO:60) | >30 µM |

Peptides in which phosphotyrosine was substituted with phosphoserine or glutamic acid did not compete with c-erbB2 for PTB domain binding (See, also FIG. 2, Panel C). Phosphorylated peptide or "phosphopeptide", PAFSPAFDNL(pY)(pY)WDQNSSEQG (SEQ ID NO:10), which had been dephosphorylated with tyrosine-specific phosphatases, also was unable to block the PTB domain/c-erbB2 interaction. This data demonstrates that the PTB domain specifically recognizes the phosphotyrosine residue.

The above data indicate that the mere presence of phosphotyrosine alone may not be the only determinant of effective PTB domain binding and competition. The truncated peptide AFDNLY(pY)WDQNS (SEQ ID NO:5), which contained a single phosphotyrosine in the second tyrosine position, had an IC$_{50}$ approximately equal to that of the double-phosphorylated peptide AFDNL(pY)(pY)WDQNS (SEQ ID NO:7) (See, FIG. 2, Panel C). However, the peptide AFDNL(pY)YWDQNS (SEQ ID NO:6), phosphorylated at only the first tyrosine residue, was 30-fold less effective in competition. While this latter peptide still shows strong inhibition of PTB domain/c-erbB2 interaction, it appears that the PTB domain binds preferentially to phosphotyrosine in the second position. Further, scrambled peptides, which contained the phosphotyrosine residues but a rearranged primary sequence, failed to compete for binding. These data demonstrate that PTB not only binds phosphotyrosine, but also recognizes a range of specific adjacent amino acids.

Accordingly, to determine which residues in the peptide PAFSPAFDNLY(pY)WDQNSSEQG were important for binding to the PTB domain, a series of peptides containing point mutations in the sequence were prepared and tested for inhibition of PTB domain/c-erbB2 binding. The results are shown in Table 4, below. The substituted residues are underlined. Relative inhibition scales denote IC$_{50}$ values of 50–500 nM ("+++"), 500 nM to 5 µM ("++") 5 to 50 µM ("+") and >50 µM ("–").

TABLE 4

| Peptide | | Inhibition |
|---|---|---|
| PAFSPAADNLY(pY)WDQNSSEQG | (SEQ ID NO:11) | ++ |
| PAFSPAFANLY(pY)WDQNSSEQG | (SEQ ID NO:14) | + |

TABLE 4-continued

| Peptide | | Inhibition |
|---|---|---|
| PAFSPAFSNLY(pY)WDQNSSEQG | (SEQ ID NO:17) | + |
| PAFSPAFDALY(pY)WDQNSSEQG | (SEQ ID NO:61) | – |
| PAFSPAFDQLY(pY)WDQNSSEQG | (SEQ ID NO:62) | – |
| PAFSPAFDDLY(pY)WDQNSSEQG | (SEQ ID NO:63) | – |
| PAFSPAFDNAY(pY)WDQNSSEQG | (SEQ ID NO:20) | ++ |
| PAFSPAFDNLAY(pY)WDQNSSEQG | (SEQ ID NO:64) | ++ |
| PAFSPAFDNLFY(pY)WDQNSSEQG | (SEQ ID NO:65) | ++ |
| PAFSPAFDNLY(pY)ADQNSSEQG | (SEQ ID NO:66) | – |
| PAFSPAFDNLY(pY)FDQNSSEQG | (SEQ ID NO:25) | ++ |

TABLE 4-continued

| Peptide | | Inhibition |
|---|---|---|
| PAFSPAFDNLY(pY)W<u>A</u><u>Q</u>NSSEQG | (SEQ ID NO:28) | +++ |
| PAFSPAFDNLY(pY)WD<u>A</u>NSSEQG | (SEQ ID NO:31) | ++ |
| PAFSPAFDNLY(pY)WD<u>N</u>NSSEQG | (SEQ ID NO:34) | ++ |
| PAFSPAFDNLY(pY)WD<u>D</u>NSSEQG | (SEQ ID NO:67) | ++ |
| PAFSPAFDNLY(pY)WD<u>Q</u>ASSEQG | (SEQ ID NO:68) | ++ |
| PAFSPAFDNLY(pY)WDQN<u>A</u>SEQG | (SEQ ID NO:43) | ++ |

From the above data, it can be seen that substitution of the asparagine in the 9th position can have a negative effect on PTB binding. Replacement of aspartic acid in the 8th position also impaired the peptides blocking ability, however this specific residue was not required for competition. Replacement of tryptophan in the 13th position with phenylalanine generally resulted in little loss of affinity, although substitution of this tryptophan with alanine resulted in reduced affinity. This suggests that large hydrophobic or aromatic residues at this position may confer higher affinity. Mutations outside of the central motif DNLY(pY)W (SEQ ID NO:74) generally resulted in only moderate losses in the affinity of the peptide.

To demonstrate directly that the phosphopeptides bind to the PTB domain, biotinylated peptides were incubated with PTB domain-containing protein ("PTB domain"). The PTB domain was immunoprecipitated and the washed pellet assayed for the presence of bound peptide with streptavidin-coupled alkaline phosphatase. PTB domain was able to bind directly to phosphorylated peptide PAFSPAFDNL(pY)(pY)WDQNSSEQG ("pY1221/pY1222") (SEQ ID NO:10), but did not bind to unphosphorylated peptide (See FIG. 3). Further, PTB domain did not bind to phosphorylated peptides containing conservative point mutations at the asparagine in the ninth position. The specificity of this sequence for PTB domain was shown by the inability of the SH2 domain of SHC to bind phosphorylated peptide PAFSPAFDNL(pY)(pY)WDQNSSEQG (SEQ ID NO:10). Additionally, this peptide also blocks association of the SHC PTB domain in vitro with pp145, a previously identified target of the SHC protein, derived from activated B cells. See, Kavanaugh and Williams, supra.

III. Peptides of the Invention

The peptides of the present invention generally comprise a core sequence which corresponds to a PTB recognition sequence motif. This general PTB recognition sequence motif can be readily identified from the above described data. Typically, the peptides will comprise the sequence motif $NX_3X_1X_2X_4$, where $X_1$ is Y, pY or an analog thereof, E, T, D, A, F or Q; $X_2$ is pY or an analog thereof, or Y, provided that at least one of $X_1$ and $X_2$ are pY, or an analog thereof; $X_3$ can be any natural or unnatural amino acid, but is preferably L or A; $X_4$ is W, F, L, S or Q (SEQ ID NO:1). Generally, this sequence motif may be present as its own peptide, or may be a core of a longer sequence. Generally, the peptides of the present invention will comprise the above motif as a portion or a whole of a peptide of from 5 to about 100 amino acids in length. Typically, the peptides will be from about 6 to about 100 amino acids in length, preferably the peptides will be from about 12 to about 100 amino acids in length, more preferably from about 12 to about 50 amino acids in length, and most preferably, from about 21 to about 50 amino acids in length.

In particularly preferred aspects of the present invention, the peptides are characterized by the core sequence of amino acids $X_5NX_3X_1X_2X_4$, where $X_1$, $X_2$, $X_3$ and $X_4$ are as described above, and $X_5$ can be any natural or unnatural amino acid, but is preferably D, E, S or A (SEQ ID NO:2). Still more preferred are peptides which comprise the core sequence of amino acids $DNX_3X_1pYX_4$ (SEQ ID NO:3)and $ENX_3X_1pYX_4$ (SEQ ID NO:4). The most preferred peptides will generally comprise one of the following core sequences of amino acids:

PAFSPAFDNLY(pY)WDQNSSEQG (SEQ ID NO:8); PAFSPAFDNL(pY)YWDQNSSEQG (SEQ ID NO:9); PAFSPAFDNL(pY)(pY)WDQNSSEQG (SEQ ID NO:10); AFDNLY(pY)WDQNS (SEQ ID NO:5); AFDNL(pY)YWDQNS(SEQ ID NO:6); AFDNL(pY)(pY)WDQNS (SEQ ID NO:7); PAFSPAADNLY(pY)WDQNSSEQG (SEQ ID NO:11); PAFSPAADNL(pY)YWDQNSSEQG (SEQ ID NO:12); PAFSPAADNL(pY)(pY)WDQNSSEQG (SEQ ID NO:13); PAFSPAFANLY(pY)WDQNSSEQG (SEQ ID NO:14); PAFSPAFANL(pY)YWDQNSSEQG (SEQ ID NO:15); PAFSPAFANL(pY)(pY)WDQNSSEQG (SEQ ID NO:16); PAFSPAFSNLY(pY)WDQNSSEQG (SEQ ID NO:17); PAFSPAFSNL(pY)YWDQNSSEQG (SEQ ID NO:18); PAFSPAFSNL(pY)(pY)WDQNSSEQG (SEQ ID NO:19); PAFSPAFDNAY(pY)WDQNSSEQG (SEQ ID NO:20); PAFSPAFDNA(pY)YWDQNSSEQG (SEQ ID NO:21); PAFSPAFDNA(pY)(pY)WDQNSSEQG (SEQ ID NO:22); PAFSPAFDNLA(pY)WDQNSSEQG (SEQ ID NO:23); PAFSPAFDNLF(pY)WDQNSSEQG (SEQ ID NO:24); PAFSPAFDNLY(pY)FDQNSSEQG (SEQ ID NO:25); PAFSPAFDNL(pY)YFDQNSSEQG (SEQ ID NO:26); PAFSPAFDNL(pY)(pY)FDQNSSEQG (SEQ ID NO:27); PAFSPAFDNLY(pY)WAQNSSEQG (SEQ ID NO:28); PAFSPAFDNL(pY)YWAQNSSEQG (SEQ ID NO:29); PAFSPAFDNL(pY)(pY)WAQNSSEQG (SEQ ID NO:30); PAFSPAFDNLY(pY)WDANSSEQG (SEQ ID NO:31); PAFSPAFDNL(pY)YWDANSSEQG (SEQ ID NO:32); PAFSPAFDNL(pY)(pY)WDANSSEQG (SEQ ID NO:33); PAFSPAFDNLY(pY)WDNNSSEQG (SEQ ID NO:34); PAFSPAFDNL(pY)YWDNNSSEQG (SEQ ID NO:35); PAFSPAFDNL(pY)(pY)WDNNSSEQG (SEQ ID NO:36); PAFSPAFDNLY(pY)WDDNSSEQG (SEQ ID NO:37); PAFSPAFDNL(pY)YWDDNSSEQG (SEQ ID NO:38); PAFSPAFDNL(pY)(pY)WDDNSSEQG (SEQ ID NO:39); PAFSPAFDNLY(pY)WDQASSEQG (SEQ ID NO:40); PAFSPAFDNL(pY)YWDQASSEQG (SEQ ID NO:41); PAFSPAFDNL(pY)(pY)WDQASSEQG (SEQ ID NO:42); PAFSPAFDNLY(pY)WDQNASEQG (SEQ ID NO:43); PAFSPAFDNL(pY)YWDQNASEQG (SEQ ID NO:44); PAFSPAFDNL(pY)(pY)WDQNASEQG (SEQ ID NO:45); AFGGAVENPE(pY)LAPRAGTASQ (SEQ ID NO:46); and EGTPTAENPE(pY)LGLDVPV (SEQ ID NO:47).

Also included within the present invention are truncated versions of the above described peptides, as well as peptides which are modified at the carboxy and/or amino terminals, e.g., amidated or acetylated, respectively.

The polypeptides of the present invention may be used as isolated polypeptides, or may exist as fusion proteins. A "fusion protein" generally refers to a composite protein made up of two or more separate, proteins which are normally not fused together as a single protein. Thus, a fusion protein may comprise a fusion of two or more similar and homologous sequences, provided these sequences are not normally fused together. Fusion proteins will generally be made by either recombinant nucleic acid methods, i.e., as a result of transcription and translation of a gene fusion comprising a segment encoding a peptide of the invention and a segment which encodes one or more heterologous proteins, or by chemical synthesis methods well known in the art.

Additionally, the polypeptides may be free in solution or may be covalently attached to a solid support. Support bound polypeptides may be particularly useful in, e.g., screening and purification applications. Suitable solid supports include those generally well known in the art, e.g., cellulose, agarose, polystyrene, divinylbenzene and the like. Many suitable solid supports are commercially available from, e.g., Sigma Chemical Co., St Louis, Mo., or Pharmacia, Uppsala, Sweden, and come prepared for immediate coupling of affinity ligands.

These fusion proteins may be prepared to exhibit a combination of properties or activities of the derivative proteins. Typical fusion proteins may include a PTB domain-binding peptide fused to a reporter polypeptide, e.g., a substrate, cofactor, inhibitor, affinity ligand, antibody binding epitope tag, or an enzyme which is capable of being assayed. Because of their ability to recognize and bind PTB domains within a protein, the peptides of the present invention may act as an affinity ligand to direct the activity of the fused protein directly to tyrosine phosphorylated proteins. In the case of a reporter peptide/PTB domain-binding peptide fusion, this allows the presence and or location of PTB domain containing proteins to be easily determined. Typical fusion partners can include bacterial β-galactosidase, trpE, protein A, β-lactamase, α-amylase, alcohol dehydrogenase and yeast α-mating factor. See, e.g., Godowski et al., *Science* 241:812–816 (1988).

The peptides of the present invention may be prepared by a variety of means, e.g., recombinant or synthetic methods. In general, techniques for recombinant production of proteins are described, for example, in Sambrook et al., *Molecular Cloning: A Laboratory Manual* (2nd ed.) Vols. 1–3, Cold Spring Harbor Laboratory, (1989). Techniques for the synthesis of polypeptides are generally described in Merrifield *J. Amer. Chem. Soc.* 85:2149–2456 (1963), Atherton et al., *Solid Phase Peptide Synthesis: A Practical Approach*, IRL Press, Oxford (1989), and Merrifield, *Science* 232:341–347 (1986).

In addition to the above peptides which consist only of naturally-occurring amino acids, peptidomimetics of the PTB domain-binding peptides are also provided. Peptide analogs are commonly used in the pharmaceutical industry as non-peptide drugs with properties analogous to those of the template peptide. These types of non-peptide compounds are termed "peptide mimetics" or "peptidomimetics" (Fauchere, J. (1986) *Adv. Drug Res.* 15:29; Veber and Freidinger (1985) *TINS* p.392; and Evans et al. (1987) *J. Med. Chem.* 30: 1229) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm peptide (i.e., a peptide that has a biological or pharmacological activity), such as naturally-occurring PTB domain-binding polypeptide, but have one or more peptide linkages optionally replaced by a linkage selected from the group consisting of: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends Pharm Sci.* (1980) pp. 463–468 (general review); Hudson, D. et al., *Int J Pept Prot Res.* (1979) 14:177–185 (—$CH_2NH$—, $CH_2CH_2$—); Spatola, A. F. et al., *Life Sci.* (1986) 38:1243–1249 (—$CH_2$—S); Hann, M. M.,*J Chem Soc Perkin Trans I* (1982) 307–314 (—CH—CH—, cis and trans); Almquist, R. G. et al., *J Med Chem* (1980) 23:1392–1398 (—$COCH_2$—); Jennings-White, C. et al., *Tetrahedron Lett.* (1982) 23:2533 (—$COCH_2$—); Szelke, M. et al., European Appln. EP 45665 (1982) CA: 97:39405 (1982) (—$CH(OH)CH_2$—); Holladay, M. W. et al., *Tetrahedron Lett.* (1983) 24:4401–4404 (—C(OH)$CH_2$—); and Hruby, V. J., *Life Sci.* (1982) 31:189–199 (—$CH_2$—S—).

Peptide mimetics may have significant advantages over peptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) (e.g., PTB domains) to which the peptidomimetic binds to produce the therapeutic effect. Derivitization (e.g., labelling) of peptidomimetics should not substantially interfere with the desired biological or pharmacological activity of the peptidomimetic. Generally, peptidomimetics of PTB domain-binding peptides will bind to the PTB domain with high affinity and possess detectable biological activity (i.e, are agonistic or antagonistic to one or more PTB domain-mediated phenotypic changes).

In a preferred aspect of the present invention, the phosphotyrosine (pY) group within the above described peptides can be substituted with an analog of phosphotyrosine which possesses a phosphate group which is nonhydrolyzable, e.g by tyrosine phosphatases. Inclusion of a nonhydrolyzable phosphotyrosine analog allows the peptides of the invention to retain binding and/or inhibitory activity for longer periods of time, in the presence of agents which may remove the phosphate group from the phosphotyrosine, e.g., tyrosine phosphatases, thereby allowing for more effective inhibition and reduced effective amounts, among other benefits. Examples of phosphotyrosine analogs having nonhydrolyzable phosphate groups include, e.g., (phosphonomethyl) phenylalanine ("Pmp"). Pmp is a phosphotyrosine analog in which the >C—O—$PO_3H_2$ group of pY has been replaced by >C—$CH_2$—$PO_3H_2$. Inclusion of this analog within sequences recognized by other phosphotyrosine binding domains yields comparable binding as with their phosphotyrosine-containing counterparts. See, Domchek, et al., Biochem. (1992) 31:9865–9870. Thus, in an aspect of the present invention, the peptides of the present invention which comprise a core sequence $NX_3X_1X_2X_4$ (SEQ ID NO:1), where $X_1$, $X_2$, $X_3$ and $X_4$ are as previously described, the phosphotyrosine residues in $X_1$ and/or $X_2$ are substituted with Pmp.

Systematic substitution of one or more amino acids of a consensus sequence with a D-amino acid of the same type (e.g., D-lysine in place of L-lysine) may also be used to generate more stable peptides. D-amino acids are generally denoted by the lower case abbreviation for the corresponding L-amino acid. In addition, constrained peptides comprising a consensus sequence or a substantially identical consensus sequence variation may be generated by methods known in the art (Rizo and Gierasch (1992) *Ann. Rev. Biochem.* 61:387; for example, by adding internal cysteine residues capable of forming intramolecular disulfide bridges which cyclize the peptide.

VI. Methods of Use

In general, the peptides of the present invention may be particularly useful as affinity ligands which are capable of binding proteins that comprise a PTB domain. Further, phosphotyrosine recognition and binding is a common mediator in cellular signaling and cellular functioning. Accordingly, the polypeptides of the present invention may find a variety of uses in diagnostic, screening and therapeutic applications related to these areas.

A. Diagnostics and Screening

In diagnostic applications, for example, the peptides of the present invention may generally be useful in methods for identifying proteins which comprise PTB domains. These methods may allow for the identification of proteins which are specifically involved in signaling pathways, such as cell activation following the binding of a ligand to a cell surface receptor. Specifically, these methods are useful in identifying downstream signals following growth factor, hormone, antibody and cytokine activation of cells. In particular, because of their specificity, the peptides of the present invention may generally be used as probes for identifying PTB domain-containing proteins.

Therefore, in one aspect, the peptides of the present invention may be used to determine whether a particular protein comprises a PTB domain. Determination of whether a protein comprises a PTB domain may be carried out by a variety of means. For example, in some instances, it may be useful to immobilize the protein to be tested upon a solid support, e.g., a microtiter well, or nitrocellulose membrane. After blocking the remaining groups on the support, the protein to be tested may be exposed to an appropriate amount of the labelled peptide, as described herein. Detection of the label bound to the test protein indicates that the protein contains a PTB domain. As a specific example, following SDS-PAGE, the gel may be electroblotted onto an appropriate solid support, e.g., a nitrocellulose or PVDF membrane. Remaining unbound regions of the membrane may then be blocked with an appropriate inert protein, e.g., bovine serum albumin, or unphosphorylated peptide. Following buffer rinses, the blot is then contacted with a peptide of the invention to which has been coupled a detectable group, e.g., a radiolabel or enzyme. Radiographs of the blot may be compared to simultaneously run, stained SDS-PAGE gels, and the label bound proteins may be identified.

Additionally, as an affinity ligand, the peptides of the present invention may also be useful in the purification of proteins which comprise a PTB domain, from a mixture of different proteins. Affinity purification of PTB domain-containing proteins may be carried out using general affinity purification methods well known in the art. For example, a peptide of the present invention may be attached to a suitable solid support, as described above.

The mixture of proteins may then be contacted with the peptide bound to the solid support, such that the peptide selectively binds the PTB domain-containing proteins present within the mixture of proteins. The bound protein can then be washed to eliminate unbound proteins. Finally, substantially pure PTB domain-containing protein may be eluted from the solid support by generally known elution protocols, e.g., washing with an excess of phosphotyrosine, which will compete with the binding of PTB to the target peptide.

As a target of PTB domain binding, the peptides of the present invention may also be used as probes in screening for compounds which may be agonists or antagonists of that binding, and more particularly, the cell signaling pathways which lead up to, and include, the binding of PTB domain to its phosphorylated ligand, e.g., SHC/c-erbB2 interactions, middle T antigen/SHC interactions, Trk/SHC interactions, and the like.

An agonist, antagonist, or test compound may be a chemical compound, a mixture of chemical compounds, a biological macromolecule, or an extract made from biological materials such as bacteria, plants, fungi, or animal cells or tissues. Test compounds may be evaluated for potential activity as agonists or antagonists of pathways which lead up to, and include the PTB domain/phosphorylated ligand interaction. Thus, an agonist or antagonist may directly affect PTB domain/phosphorylated ligand interaction, or alternatively, may act upon an upstream event in the pathway, whereby the level of PTB domain/phosphorylated ligand interaction is affected.

Thus, an "agonist" of the pathway will enhance the level of PTB domain/phosphorylated ligand interaction, while an "antagonist" will diminish the level of that interaction. The terms "agonist" and "antagonist", as used herein, do not imply a particular mechanism of function.

In screening embodiments, the polypeptides of the present invention may be used as a model in vitro system for determining whether a test compound is an agonist or antagonist of the binding of the PTB domain to its target recognition sequence motif. Such a system permits the screening of a large number of potential drugs, or drug candidates, for the ability to enhance or inhibit PTB domain/phosphorylated ligand interactions, and resulting associated downstream events.

The screening methods comprise providing a polypeptide which contains a PTB domain, and a peptide of the present invention, whereby the protein and peptide form a complex. The complex may then be incubated with a test compound. Binding between the PTB domain and the peptide may then be determined. An increase or decrease in the level of binding between the PTB domain-containing protein and the peptide of the invention in response to a particular compound would indicate that the test compound is an agonist or antagonist of that binding, respectively. In some cases, it may be desirable to preincubate the PTB domain-containing protein, or the peptide of the invention with the test compound, prior to introduction of the peptide of the invention. The duration and conditions of preincubation will generally vary depending upon the compound being tested. Further, other reaction conditions of the preincubation, e.g., pH and salt concentration, will generally correspond to the conditions which are most effective for PTB domain binding to the peptide. Accordingly, these conditions will likely reflect the conditions normal to the particular cell-line from which the PTB domain was derived.

For many of the methods described herein, the peptides of the invention, or the PTB domain, may be covalently attached or linked to a detectable group, or label, to facilitate screening and detection. Useful detectable groups, or labels, are generally well known in the art. For example, a detectable group may be a radiolabel, such as, $^{125}$I, $^{32}$P or $^{35}$S, or a fluorescent or chemiluminescent group. Alternatively, the detectable group may be a substrate, cofactor, inhibitor, affinity ligand, antibody binding epitope tag, or an enzyme which is capable of being assayed. Suitable enzymes include, e.g., horseradish peroxidase, luciferase, or other readily assayable enzymes. These enzyme groups may be attached to the peptide by chemical means or expressed recombinantly, as a fusion protein, by methods well known in the art.

It may also be desirable to provide the peptide or PTB domain-containing protein immobilized upon a solid support, to facilitate screening of test compounds. Examples of suitable solid supports include agarose, cellulose, dextran, Sephadex™, Sepharose™, carboxymethyl cellulose, polystyrene, filter paper, nitrocellulose, ion exchange resins, plastic films, glass beads, polyaminemethylvinylether maleic acid copolymer, amino acid copolymer, ethylene-maleic acid copolymer, nylon, silk, etc. The support may be in the form of, e.g., a test tube, microtiter plate, resins, beads, test strips, or the like. The coupling of the peptide or PTB domain-containing protein with the particular solid support may be carried out by methods well known in the art.

As a specific example, a PTB domain-containing protein may be coupled to the wells of a microtiter plate. The test compound may then be added to the well of the microtiter plate to preincubate with the PTB domain-containing protein. The peptide of the invention, to which a detectable group has been attached, may then be added to the microtiter well. Following sufficient incubation, the wells may be rinsed, and binding of the peptide to the PTB domain may be assessed, e.g., by assaying for the presence of residual detectable groups. Those of skill in the art will recognize that the screening assay format may be set up in either direction, i.e., either the peptide or the PTB domain-containing protein may be bound to the support, while the other is labeled. The level of binding may then be compared to suitable positive and negative controls. Alternatively, by providing the polypeptide containing the PTB domain, and/or the peptide in known concentrations, one can assay for free, or unbound PTB domain and/or peptide, and by negative implication, determine the level of PTB domain/peptide complex which is formed.

The amount or concentration of agonist/antagonist added will, when known, vary depending on the compound, but will generally range from about 10 $\mu$M to 100 $\mu$M. Typically, a range of concentrations will be used. In the case of uncharacterized test compounds it may not be possible, and it is not necessary, to determine the concentration of agonist/antagonist.

It will also be desirable to include various experimental controls in the above assay. Examples of appropriate controls include negative controls and positive controls. In testing for agonist activity, negative controls can include incubation of cells with inert compounds (i.e., compounds known not to have agonist activity) or in the absence of added compounds. Positive controls can include incubation with compounds known to have agonist activity (e.g., the natural ligand). Logically, similar (though complementary) controls can be included in assays for antagonist activity, as will be apparent to one of ordinary skill in the art of biology, as will various additional controls. The description of controls is meant to be illustrative and in no way limiting.

In an alternative embodiment, the peptides of the present invention may be useful in modelling small molecules which interfere with PTB binding in vivo. In particular, the structure of the PTB domain recognition sequence motif, as described herein, may be applied in generating synthetic analogs and mimics of the PTB domain recognition sequence. Synthetic elements may be pieced together based upon their analogy to the structural and chemical aspects of the PTB recognition sequence motif. Such mimics and analogs may be used in blocking or inhibiting specific aspects of the cell signaling pathways, e.g., growth factor activation, and may therefore be useful as therapeutic treatments according to the methods described herein.

B. Therapeutic Applications

In addition to the above described uses, the polypeptides of the present invention, or analogs thereof, may also be used in therapeutic applications for the treatment of human or non-human mammalian patients.

PTB domain-containing proteins have been shown to bind proteins which are phosphorylated in response to the activation of a cell by various growth factors. See Kavanaugh and Williams, supra. Accordingly, the polypeptides of the present invention may be used to inhibit or block the interaction of PTB domain-containing proteins with their phosphorylated ligands by competing with those ligands.

In particular, the peptides of the present invention can be used to block or inhibit growth factor dependent activation or stimulation of cells, or more specifically, inhibit or block growth factor initiated mitogenesis. These methods may generally be used in the treatment of a variety of proliferative cell disorders, or in screening compounds effective for such treatment. "Proliferative cell disorder" refers generally to disorders which are characterized by excessive stimulation or activation of the mitogenic signaling pathways resulting in excessive or abnormal cell growth and/or differentiation. Specific disorders include, e.g., atherosclerosis, inflammatory joint diseases, psoriasis, restinosis following angioplasty, and cancer. The methods and compositions of the present invention may be particularly useful in the case of cancers where there are deregulated tyrosine kinases, such as thyroid, breast carcinoma, stomach cancer and neuroblastoma. Alternatively, the methods and compositions may be useful as a prophylactic treatment, or in screening for compounds effective in prophylactic treatments. Such prophylactic treatments will generally be administered to inhibit or block "normal" cell proliferation, for example, in immunosuppression to prevent graft rejection, and to alleviate allergic responses involving mast cell activation.

In a particularly preferred aspect, the peptides of the present invention are be used to block or inhibit the interaction between PTB domain containing proteins and the product of the c-erbB2 oncogene. More specifically, the peptides can be used to block or inhibit the interaction between the SHC protein and c-erbB2.

Gene amplification of c-erbB2 is known to result in overexpression of the c-erbB2 product in a variety of adenocarcinomas, and a number of studies link this overexpression to the neoplastic process. c-erbB2 amplification has been described as being associated with human gastric tumor, non-small cell lung, colon, ovarian and pancreatic adenocarcinomas. Overexpression of c-erbB2 product has also been found in a significant percentage of breast carcinomas. For a review of c-erbB2, see Dougall, et al., *Oncogene* (1994) 9:2109–2123.

Studies have demonstrated the relationship between c-erbB2 overexpression and cellular transformation, using monoclonal antibodies. Antibodies to the c-erbB2 protein, as well as its murine homolog, have proven effective in inhibiting tumor formation, or otherwise shown antiproliferative effects. These studies indicate that the continued expression of the c-erbB2 product is necessary for the maintenance of the neoplastic phenotype in c-erbB2 transformed cells, and that expression of the c-erbB2 product can be functionally linked to cellular transformation. Dougall, et al. Further, studies indicate that several critical tyrosine residues within the c-erbB2 protein are important for conveying the mitogenic signals of the c-erbB2 protein. The peptides of the present invention are particularly useful in blocking these phosphotyrosine mediated mitogenic signals.

The use of the peptides of the invention in methods for inhibiting or blocking c-erbB2/PTB domain interaction can be useful in the treatment of disorders which result from the overexpression of the c-erbB2 gene product, including, e.g., human gastric tumor, non-small cell lung, colon, ovarian and pancreatic adenocarcinomas, as well as breast carcinomas. Typically, such treatment will comprise administering to a patient suffering from one of the above disorders, an effective amount of a polypeptide of the present invention, generally in combination with a pharmaceutically acceptable carrier.

It will also be appreciated by those of skill in the art, that peptidomimetics of the present invention may also be effective in blocking growth factor dependent activation of cells, or PTB domain/c-erbB2 interaction. Specifically, synthetic analogs to the PTB domain recognition motif as described herein, may also be applied in the treatment methods described.

The quantities of reagents necessary for effective therapy, also referred to herein as an "effective amount," or "therapeutically effective amount," will depend upon many different factors, including means of administration, target site, physiological state of the patient and other medicants administered. Thus, treatment doses will need to be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Generally, therapeutically effective amounts of the peptides of the present invention will be from about 0.0001 to about 100 mg/kg, and more usually, from about 0.001 to about 0.1 mg/kg of the host's body weight. Various considerations are described, e.g., in Gilman et al., (Eds.), *Goodman and Gilman's: The Pharmacological Basis of Therapeutics*, (8th ed. 1990), Pergamon Press, and *Remington's Pharmaceutical Sciences* (7th ed. 1985) Mack Publishing Co., Easton, Penn. Methods of administration, also discussed in the above references, include, e.g., oral, intravenous, intraperitoneal or intramuscular administration, and local administration, including topical, transdermal diffusion and aerosol administration, for therapeutic, and/or prophylactic treatment.

While it is possible to administer the active ingredient alone, it is preferable to present it as part of a pharmaceutical composition or formulation. These formulations comprise the peptides and/or analogs of the invention in a therapeutically or pharmaceutically effective dose together with one or more pharmaceutically or therapeutically acceptable carriers and optionally other ingredients, e.g., other therapeutic ingredients, or additional constituents which may be required to approximate physiological conditions, such as pH adjusting and buffering agents, tonicity adjusting agents, wetting agents and the like. Additional constituents of the pharmaceutical compositions may include those generally known in the art for the various administration methods used, e.g., oral forms may contain flavorants, sweeteners and the like. For solid compositions, conventional nontoxic solid carriers may be used which include, e.g., pharmaceutical grades of mannitol, lactose, starch, magnesium stearate, sodium saccharin, talcum, cellulose, glucose, sucrose, magnesium carbonate and the like. Various considerations are described, e.g., in Gilman et al. (eds) (1990) *Goodman and Gilman's: The Pharmacological Bases of Therapeutics,* 8th Ed., Pergamon Press; *Novel Drug Delivery Systems,* 2nd Ed., Norris (ed.) Marcel Dekker Inc. (1989), and *Remington's Pharmaceutical Sciences.*

Methods for administration are also discussed in the above references, e.g., for oral, intravenous, intraperitoneal, or intramuscular administration, and others. Pharmaceutically acceptable carriers will include water, saline, buffers, and other compounds described, e.g., in the *Merck Index,* Merck & Co., Rahway, N.J. See, also, *Bioreversible Carriers in Drug Design, Theory and Application,* Roche (ed.), Pergamon Press, (1987). For some methods of administration, e.g., oral, it may be desirable to provide the active ingredient in a liposomal formulation. This is particularly desirable where the active ingredient may be subject to degradative environments, for example, proteolytic digestive enzymes. Liposomal formulations are well known in the art, and are discussed in, e.g., *Remington's Pharmaceutical Sciences*, supra. Administration may also be carried out by way of a controlled release composition or device, whereby a slow release of the active ingredient allows continuous administration over a longer period of time.

The present invention is further illustrated by the following examples. These examples are merely to illustrate aspects of the present invention and are not intended as limitations of this invention.

EXAMPLES

Example 1

Expression Cloning of Tyrosine-Phosphorylated Targets of a PTB Domain

Sf9 cells expressing residues 526 to 1067 of mouse PDGF receptor cytoplasmic domain (tyrosine kinase) in recombinant baculovirus were prepared and lysed as described by Kavanaugh and Williams, *Science* (1994) 266:1862–1865, and Collawn, et al., (1990) *Cell* 63:1061–1072. $1.1 \times 10^6$ plaques of an oligo-dT primed Balb/c 3T3 fibroblast cDNA λ gt11 library were plated and transferred to IPTG-impregnated PVDF filters using standard techniques. See, Sambrook, et al. Molecular Cloning: A Laboratory Manual (Cold Spring Harbor Laboratory Press, New York, 2nd ed., 1989). The filters were blocked in TBSTM, 5% BSA (20 mM Tris-HCl, pH 7.4, 137 mM NaCl, 10 mM $MgCl_2$ and 0.1% Triton X-100) and then incubated in TBSTM containing one fifth volume PDGF receptor cytoplasmic domain lysate, 250 μM ATP and 1 mM sodium orthovanadate at room temperature for 30 minutes. The filters were washed and incubated with $^{32}$P-labeled GST-PTB domain fusion protein as described in Kavanaugh and Williams, supra.

Example 2

Association of c-erbB2 with PTB Domain

Influenza hemagglutinin (IHA) tagged GST-PTB domain fusion proteins were expressed from recombinant baculovirus in sf9 cells. Sf9 cells or confluent SKBR3 cells were lysed in 2× hybridization buffer containing protease inhibitors and 1 mM sodium orthovanadate, as described in Kavanaugh and Williams, *Science* (1994) 266:1862–1865. Approximately 100 ng of GST-PTB domain was incubated with 1 μg of total SKBR3 lysate protein in 1× hybridization buffer for 30 minutes at 4° C., immunoprecipitated with 2 μg of 12CA5 and protein-A sepharose, and the pellets washed 3 to 5 times prior to immunoblot analysis with anti c-neu/c-erbB2 antibodies. The results are shown in FIG. 2A. Equal amounts of GST-PTB domain protein were immunoprecipitated as determined by immunoblotting with 12CA5.

Example 3
Inhibition of PTB/c-erbB2 Interaction

IHA-tagged GST-PTB fusion protein was incubated with SKBR3 lysate as described above, in the presence and absence of the peptides pY1112, pY1127, pY1139, pY1196, pY1221/pY1222 and pY1248. The mixture was immunoprecipitated with 12CA5, and immunoblotted with anti-c-neu/c-erbB2 antibodies. These results are shown in FIG. 2B. PTB domain was pre-incubated with the indicated concentrations of peptide for 30 minutes at 4° C. prior to adding SKBR3 cell lysate. This experiment was repeated with varying concentrations of the peptide pY1221/pY1222 and the results are shown in FIG. 2B, lower blot. Substantial inhibition is shown at as low as 50 nM peptide concentration. This experiment was also repeated using the peptides shown in Table 3, and the results are shown in FIG. 2C. Of the peptides tested, peptides pY1221/pY1222 and Y1221/pY1222 appear to completely block PTB/c-erbB2 interaction, whereas peptide pY1221/Y1222 showed some inhibition of this interaction. In the experiments involving serine-phosphorylated peptides, 1 μM okadaic acid and 1 mM EGTA were included in the buffers. Peptides were synthesized as described by Escobedo, et al., *Mol. Cell. Biol.* (1991) 11:1125–1132, and HPLC purified. In this latter experiment, 300 nM peptides were used.

Example 4
Binding of Phosphopeptides to PTB Domain

Peptides were biotinylated during synthesis and HPLC purified. 100 ng of GST-PTB domain or GST-SH2 domain fusion protein were incubated in 1× hybridization buffer with 500 nM biotinylated phosphopeptide for 1 hour at 4° C., immunoprecipitated as described in Example 2, above, washed once, and the pellets incubated with 0.25 units of streptavidin-alkaline phosphatase for 5 minutes at 4° C. The pellets were washed twice more, incubated for 3 minutes at room temperature with 1 mg/ml p-nitrophenylphosphate in 100 mM glycine, pH 10.1, 1 mN $ZnCl_2$ and 1 mM $MgCl_2$. The absorbance was measured at 405 nm.

Figure 3:
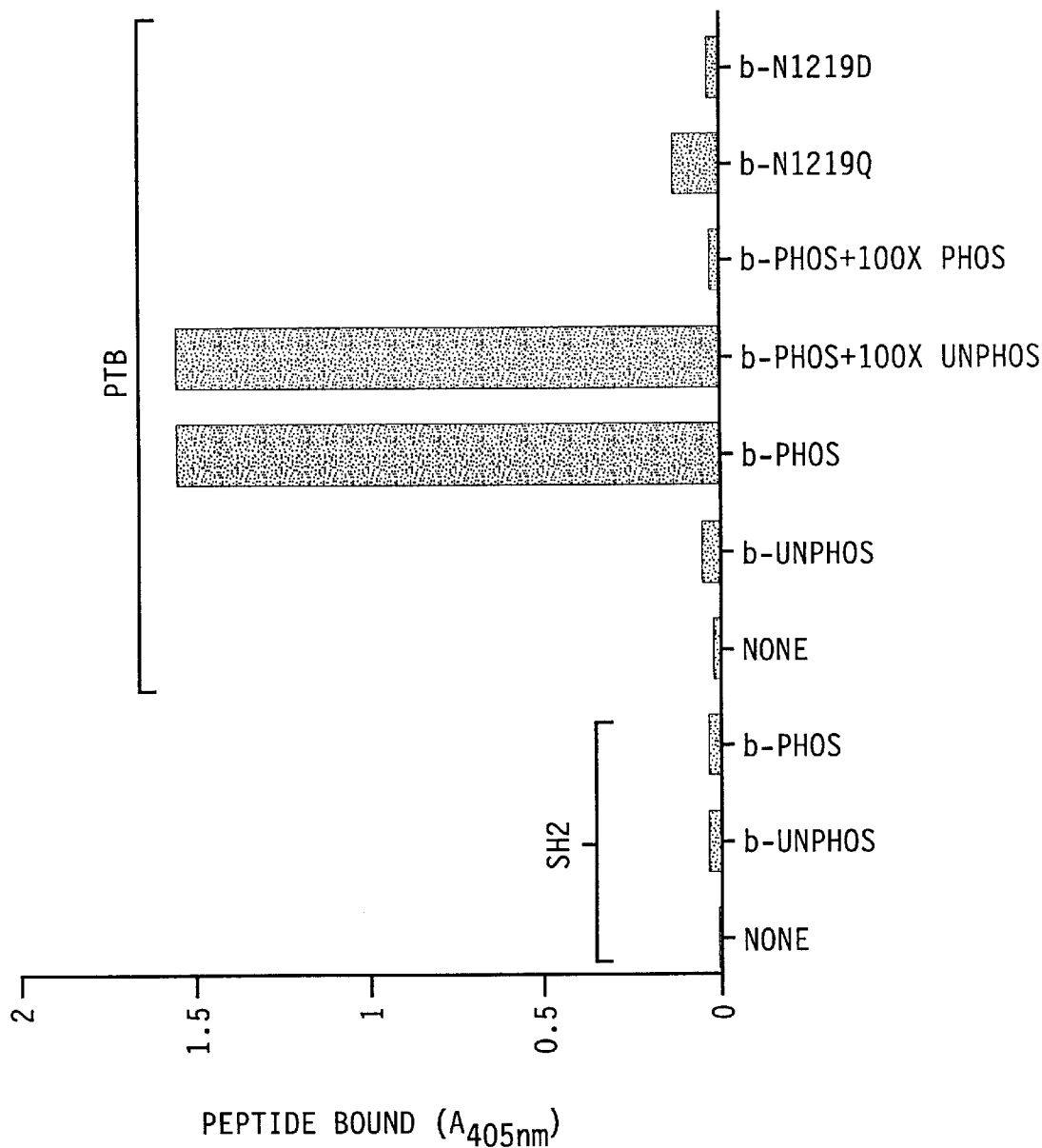
FIG. 3 is a bar graph showing the effects of various conditions upon PTB domain/phosphopeptide binding. IHA tagged GST-PTB domain fusion protein was incubated in the presence of the following biotinylated peptides: PAFS-PAFDNLYYWDQNSSEQG ("b-unphos.") (SEQ ID NO:48); PAFSPAFDNL(pY)(pY)WDQNSSEQG ("b-phos.") (SEQ ID NO:10), alone and in the presence of 100× non-biotinylated, unphosphorylated and phosphorylated peptide ("100× unphos." and "100× phos.", respectively); PAFSPAFDQL(pY)(pY)WDQNSSEQG ("b-N1219Q") (SEQ ID NO:72); and PAFSPAFDDL(pY)(pY) WDQNSSEQG ("b-N1219D") (SEQ ID NO:73). Specific binding was detected using streptavidin-coupled alkaline phosphatase. Also shown is the level of binding by b-phos. and b-unphos. to an SH2 phosphotyrosine binding domain.

The direct binding of the phosphorylated peptide PAFSPAFDNL(pY)(pY)WDQNSSEQG ("b-phos.") (SEQ ID NO:10) to the PTB domain is shown in FIG. 3. This peptide bound the PTB domain both in the presence and absence of a 100× concentration of unphosphorylated, non-biotinylated peptide. PTB binding was inhibited in the presence of 100× concentration of phosphorylated peptide, which competed for the PTB domain. Unphosphorylated, biotinylated peptide did not bind the PTB domain. Neither the phosphorylated nor unphosphorylated form of this peptide were able to specifically bind to an SH2 domain.

The peptides PAFSPAFDQL(pY)(pY)WDQNSSEQG ("b-N1219Q") (SEQ ID NO:72) and PAFSPAFDDL(pY)(pY)WDQNSSEQG ("b-N1219D") (SEQ ID NO:73) which carried point mutations in the asparagine residue in the ninth position, also show substantially reduced binding to the PTB domain in these assays (FIG. 3).

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

---

What is claimed is:

1. A substantially pure peptide which is capable of binding a PTB phosphotyrosine binding domain, wherein the peptide is from 5 to about 21 amino acids in length, and comprises a core sequence of amino acids Asn-$X_3$-$X_1$-$X_2$-$X_4$ (SEQ ID NO:1);

wherein $X_1$ is selected from the group consisting of Tyr, phosphotyrosine or an analog thereof, Thr, Asp, Gln, Ala and Phe;

$X_2$ is selected from phosphotyrosine or an analog thereof, and Tyr, provided that at least one of $X_1$ and $X_2$ is phosphotyrosine, or an analog thereof;

$X_3$ is selected from the group consisting of Leu and Ala; and $X_4$ is selected from the group consisting of Trp, Leu, Ser, Phe and Gln.

2. The peptide as recited in claim 1, wherein the peptide is from 6 to about 21 amino acids in length, and comprises a core sequence of amino acids $X_5$-Asn-$X_3$-$X_1$$X_2$-$X_4$ (SEQ ID NO:2), wherein $X_5$ is selected from the group consisting of Asp, Ser, Glu and Ala.

3. The peptide as recited in claim 2, wherein $X_2$ is phosphotyrosine.

4. The peptide as recited in claim 1, wherein the peptide is from 6 to about 21 amino acids in length, and comprises a core sequence of amino acids selected from the group consisting of Asp-Asn-$X_3$-$X_1$-phosphotyrosine-$X_4$ (SEQ ID NO:3) and Glu-Asn-$X_3$-$X_1$-phosphotyrosine-$X_4$ (SEQ ID NO:4), where $X_4$ is selected from the group consisting of Trp and Phe.

5. The peptide as recited in claim 1, wherein the peptide is from 12 to about 21 amino acids in length, and comprises a core sequence of amino acids selected from the group consisting of SEQ ID NOS: 5–7.

6. The peptide as recited in claim 1, wherein at least one of $X_1$ and $X_2$ is an analog of phosphotyrosine, and said analog is (phosphonomethyl)phenylalanine.

7. A composition comprising a peptide as recited in claim 1, and a pharmaceutically acceptable carrier.

8. A method of determining whether a protein comprises a PTB phosphotyrosine binding domain, comprising the steps of:

contacting the protein with a peptide of claim 1, and determining whether the peptide binds to the protein during said contacting step, and correlating said binding of the peptide to the protein to the presence of a PTB phosphotyrosine binding domain in the protein.

9. The method as recited in claim 8, wherein prior to said contacting step, the protein is attached to a solid support;

the peptide used in said contacting step further comprises a detectable group fused to the peptide; and said determining step comprises assaying for the presence of the detectable group.

10. The method as recited in claim 8, wherein prior to said contacting step, the peptide is attached to a solid support.

11. A method of determining whether a test compound is an agonist or antagonist of a PTB phosphotyrosine binding domain/phosphorylated ligand interaction, comprising the steps of:

incubating the test compound with a protein comprising a PTB phosphotyrosine binding domain and a peptide of claim 1, and determining the amount of protein bound to the peptide during said incubating step; and comparing the amount of protein bound to the peptide during said incubating step to an amount of protein bound to the peptide in the absence of the test compound, identifying the test compound as an agonist of a PTB phosphotyrosine binding domain/phosphorylated ligand interaction when there is an increase in the amount of protein bound to the peptide in the presence of the test compound, and identifying the test compound as an antagonist of a PTB phosphotyrosine binding domain/phosphorylated ligand interaction when there is a decrease in the amount of protein bound to the peptide in the presence of the test compound.

12. A method of inhibiting the binding of a PTB phosphotyrosine binding domain-containing protein to a tyrosine phosphorylated target, comprising contacting the PTB phosphotyrosine binding domain-containing protein with an effective amount of the peptide of claim 1.

13. The method as recited in claim 12, wherein the tyrosine phosphorylated target is c-erbB2.

14. The method as recited claim 13, wherein the PTB phosphotyrosine binding domain-containing protein is SHC.

15. A method of obtaining substantially pure PTB phosphotyrosine binding-domain-containing protein from a mixture of different proteins, comprising the steps of:

providing a peptide of claim 1 bound to a solid support;

contacting the mixture of different proteins with the peptide bound to the solid support whereby the PTB phosphotyrosine binding domain-containing protein is bound to the peptide;

washing the solid support to remove unbound proteins; and eluting substantially pure PTB phosphotyrosine binding-domain-containing protein from the solid support.

16. The peptide of claim 1 that is from 12 to 21 amino acids in length.

17. A substantially pure peptide which is capable of binding a PTB phosphotyrosine binding domain, wherein the peptide is from 21 to about 50 amino acids in length, and comprises a core sequence of amino acids selected from the group consisting of SEQ ID NOS: 8–45.

18. A substantially pure peptide which is capable of binding a PTB phosphotyrosine binding domain, wherein the peptide is from 21 to about 50 amino acids in length and which comprises a core sequence of amino acids selected from the group consisting of SEQ ID NOS:46–47.

19. A method of determining whether a test compound is an agonist or antagonist of a PTB phosphotyrosine binding domain/phosphorylated ligand interaction, comprising the steps of:

incubating the test compound with a protein comprising a PTB phosphotyrosine binding domain and a peptide, which peptide is from about 21 to about 50 amino acid residues in length and which comprises a core amino acid sequence selected from SEQ ID NOS:8–47; and determining the amount of protein bound to the peptide during said incubating I step; and comparing the amount of protein bound to the peptide during said incubating step to an amount of protein bound to the peptide in the absence of the test compound, wherein a test compound is determined to be an agonist of a PTB phosphotyrosine binding domain/phosphorylated ligand interaction when there is an increase in the amount of protein bound to the peptide in the presence of the test compound, and a test compound is determined to be an antagonist of a PTB phosphotyrosine binding domain/phosphorylated ligand interaction when there is a decrease in the amount of protein bound to the peptide in the presence of the test compound.

* * * * *

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: one-of(2)
      (D) OTHER INFORMATION: /note= "Xaa is Leu or Ala."

(ix) FEATURE:
      (A) NAME/KEY: Region
      (B) LOCATION: one-of(3)
      (D) OTHER INFORMATION: /note= "Xaa is Tyr, phosphotyrosine or
         analogs thereof, Glu, Thr, Asp, Gln, Ala or Phe."

(ix) FEATURE:
      (A) NAME/KEY: Region
      (B) LOCATION: one-of(4)
      (D) OTHER INFORMATION: /note= "Xaa is Tyr, phosphotyrosine or
         analogs thereof."

(ix) FEATURE:
        (A) NAME/KEY: Region
        (B) LOCATION: one-of(5)
        (D) OTHER INFORMATION: /note= "Xaa is Trp, Leu, Ser, Phe or
            Gln."

(xi) SEQUENCE DESCRIPTION: SEQ ID NO:1:

Asn Xaa Xaa Xaa Xaa
1               5

(2) INFORMATION FOR SEQ ID NO:2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(1)
        (D) OTHER INFORMATION: /note= "Xaa is Asp, Ser, Glu or Ala."

(ix) FEATURE:
        (A) NAME/KEY: Region
        (B) LOCATION: one-of(3)
        (D) OTHER INFORMATION: /note= "Xaa is Leu or Ala."

(ix) FEATURE:
        (A) NAME/KEY: Region
        (B) LOCATION: one-of(4)
        (D) OTHER INFORMATION: /note= "Xaa is Tyr, phosphotyrosine or
            analogs thereof, Glu, Thr, Asp, Gln, Ala or Phe."

(ix) FEATURE:
        (A) NAME/KEY: Region
        (B) LOCATION: one-of(5)
        (D) OTHER INFORMATION: /note= "Xaa is Tyr, phosphotyrosine or
            analogs thereof."

(ix) FEATURE:
        (A) NAME/KEY: Region
        (B) LOCATION: one-of(6)
        (D) OTHER INFORMATION: /note= "Xaa is Trp, Leu, Ser, Phe or
            Gln."

(xi) SEQUENCE DESCRIPTION: SEQ ID NO:2:

Xaa Asn Xaa Xaa Xaa Xaa
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(3)
        (D) OTHER INFORMATION: /note= "Xaa is Leu or Ala."

(ix) FEATURE:
        (A) NAME/KEY: Region
        (B) LOCATION: one-of(4)
        (D) OTHER INFORMATION: /note= "Xaa is Tyr, phosphotyrosine or
            analogs thereof, Glu, Thr, Asp, Gln, Ala or Phe."

```
      (ix) FEATURE:
           (A) NAME/KEY: Region
           (B) LOCATION: one-of(5)
           (D) OTHER INFORMATION: /note= "Xaa is Tyr, phosphotyrosine or
               analogs thereof."

(ix) FEATURE:
           (A) NAME/KEY: Region
           (B) LOCATION: one-of(6)
           (D) OTHER INFORMATION: /note= "Xaa is Trp or Phe."

(xi) SEQUENCE DESCRIPTION: SEQ ID NO:3:

Asp Asn Xaa Xaa Xaa Xaa
1               5

(2) INFORMATION FOR SEQ ID NO:4:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Region
           (B) LOCATION: one-of(3)
           (D) OTHER INFORMATION: /note= "Xaa is Leu or Ala."

(ix) FEATURE:
           (A) NAME/KEY: Region
           (B) LOCATION: one-of(4)
           (D) OTHER INFORMATION: /note= "Xaa is Tyr, phosphotyrosine or
               analogs thereof, Glu, Thr, Asp, Gln, Ala or Phe."

(ix) FEATURE:
           (A) NAME/KEY: Region
           (B) LOCATION: one-of(5)
           (D) OTHER INFORMATION: /note= "Xaa is Tyr, phosphotyrosine or
               analogs thereof."

(ix) FEATURE:
           (A) NAME/KEY: Region
           (B) LOCATION: one-of(6)
           (D) OTHER INFORMATION: /note= "Xaa is Trp or Phe."

(xi) SEQUENCE DESCRIPTION: SEQ ID NO:4:

Glu Asn Xaa Xaa Xaa Xaa
1               5

(2) INFORMATION FOR SEQ ID NO:5:

(i) SEQUENCE CHARACTERISTICS:
           (A) LENGTH: 12 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Region
           (B) LOCATION: one-of(7)
           (D) OTHER INFORMATION: /note= "Xaa is phosphotyrosine."

(xi) SEQUENCE DESCRIPTION: SEQ ID NO:5:

Ala Phe Asp Asn Leu Tyr Xaa Trp Asp Gln Asn Ser
1               5                   10
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(6)
        (D) OTHER INFORMATION: /note= "Xaa is phosphotyrosine."

(xi) SEQUENCE DESCRIPTION: SEQ ID NO:6:

```
Ala Phe Asp Asn Leu Xaa Tyr Trp Asp Gln Asn Ser
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(6,7)
        (D) OTHER INFORMATION: /note= "Xaa is phosphotyrosine."

(xi) SEQUENCE DESCRIPTION: SEQ ID NO:7:

```
Ala Phe Asp Asn Leu Xaa Xaa Trp Asp Gln Asn Ser
1               5                   10
```

(2) INFORMATION FOR SEQ ID NO:8:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:8:

```
Pro Ala Phe Ser Pro Ala Phe Asp Asn Leu Tyr Xaa Trp Asp Gln Asn
1               5                   10                  15

Ser Ser Glu Gln Gly
            20
```

(2) INFORMATION FOR SEQ ID NO:9:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Region
    (B) LOCATION: one-of(11)
    (D) OTHER INFORMATION: /note= "Xaa is phosphotyrosine."

(xi) SEQUENCE DESCRIPTION: SEQ ID NO:9:

Pro Ala Phe Ser Pro Ala Phe Asp Asn Leu Xaa Tyr Trp Asp Gln Asn
1               5                   10                  15

Ser Ser Glu Gln Gly
            20

(2) INFORMATION FOR SEQ ID NO:10:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:10:

Pro Ala Phe Ser Pro Ala Phe Asp Asn Leu Xaa Xaa Trp Asp Gln Asn
1               5                   10                  15

Ser Ser Glu Gln Gly
            20

(2) INFORMATION FOR SEQ ID NO:11:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:11:

Pro Ala Phe Ser Pro Ala Ala Asp Asn Leu Tyr Xaa Trp Asp Gln Asn
1               5                   10                  15

Ser Ser Glu Gln Gly
            20

(2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:12:

Pro Ala Phe Ser Pro Ala Ala Asp Asn Leu Xaa Tyr Trp Asp Gln Asn
1               5                   10                  15

Ser Ser Glu Gln Gly
            20

(2) INFORMATION FOR SEQ ID NO:13:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:13:

Pro Ala Phe Ser Pro Ala Ala Asp Asn Leu Xaa Xaa Trp Asp Gln Asn
1               5                   10                  15

Ser Ser Glu Gln Gly
            20

(2) INFORMATION FOR SEQ ID NO:14:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:14:

Pro Ala Phe Ser Pro Ala Phe Ala Asn Leu Tyr Xaa Trp Asp Gln Asn
1               5                   10                  15

Ser Ser Glu Gln Gly
            20

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:15:

Pro Ala Phe Ser Pro Ala Phe Ala Asn Leu Xaa Tyr Trp Asp Gln Asn
1               5                   10                  15

Ser Ser Glu Gln Gly
            20

(2) INFORMATION FOR SEQ ID NO:16:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:16:

```
Pro Ala Phe Ser Pro Ala Phe Ala Asn Leu Xaa Xaa Trp Asp Gln Asn
1               5                   10                  15

Ser Ser Glu Gln Gly
            20
```

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:17:

```
Pro Ala Phe Ser Pro Ala Phe Ser Asn Leu Tyr Xaa Trp Asp Gln Asn
1               5                   10                  15

Ser Ser Glu Gln Gly
            20
```

(2) INFORMATION FOR SEQ ID NO:18:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:18:

```
Pro Ala Phe Ser Pro Ala Phe Ser Asn Leu Xaa Tyr Trp Asp Gln Asn
1               5                   10                  15

Ser Ser Glu Gln Gly
            20
```

(2) INFORMATION FOR SEQ ID NO:19:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Region
    (B) LOCATION: one-of(12)
    (D) OTHER INFORMATION: /note= "Xaa is phosphotyrosine."

(xi) SEQUENCE DESCRIPTION: SEQ ID NO:19:

Pro Ala Phe Ser Pro Ala Phe Ser Asn Leu Xaa Xaa Trp Asp Gln Asn
1               5                   10                  15

Ser Ser Glu Gln Gly
            20

(2) INFORMATION FOR SEQ ID NO:20:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:20:

Pro Ala Phe Ser Pro Ala Phe Asp Asn Ala Tyr Xaa Trp Asp Gln Asn
1               5                   10                  15

Ser Ser Glu Gln Gly
            20

(2) INFORMATION FOR SEQ ID NO:21:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:21:

Pro Ala Phe Ser Pro Ala Phe Asp Asn Ala Xaa Tyr Trp Asp Gln Asn
1               5                   10                  15

Ser Ser Glu Gln Gly
            20

(2) INFORMATION FOR SEQ ID NO:22:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:22:

Pro Ala Phe Ser Pro Ala Phe Asp Asn Ala Xaa Xaa Trp Asp Gln Asn
1               5                   10                  15

Ser Ser Glu Gln Gly
            20

(2) INFORMATION FOR SEQ ID NO:23:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:23:

Pro Ala Phe Ser Pro Ala Phe Asp Asn Leu Ala Xaa Trp Asp Gln Asn
1               5                   10                  15

Ser Ser Glu Gln Gly
            20

(2) INFORMATION FOR SEQ ID NO:24:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:24:

Pro Ala Phe Ser Pro Ala Phe Asp Asn Leu Phe Xaa Trp Asp Gln Asn
1               5                   10                  15

Ser Ser Glu Gln Gly
            20

(2) INFORMATION FOR SEQ ID NO:25:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:25:

Pro Ala Phe Ser Pro Ala Phe Asp Asn Leu Tyr Xaa Phe Asp Gln Asn
1               5                   10                  15

Ser Ser Glu Gln Gly
            20

(2) INFORMATION FOR SEQ ID NO:26:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:26:

```
Pro Ala Phe Ser Pro Ala Phe Asp Asn Leu Xaa Tyr Phe Asp Gln Asn
1               5                   10                  15

Ser Ser Glu Gln Gly
            20
```

(2) INFORMATION FOR SEQ ID NO:27:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:27:

```
Pro Ala Phe Ser Pro Ala Phe Asp Asn Leu Xaa Xaa Phe Asp Gln Asn
1               5                   10                  15

Ser Ser Glu Gln Gly
            20
```

(2) INFORMATION FOR SEQ ID NO:28:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:28:

```
Pro Ala Phe Ser Pro Ala Phe Asp Asn Leu Tyr Xaa Trp Ala Gln Asn
1               5                   10                  15

Ser Ser Glu Gln Gly
            20
```

(2) INFORMATION FOR SEQ ID NO:29:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
            (A) NAME/KEY: Region
            (B) LOCATION: one-of(11)
            (D) OTHER INFORMATION: /note= "Xaa is phosphotyrosine."

(xi) SEQUENCE DESCRIPTION: SEQ ID NO:29:

Pro Ala Phe Ser Pro Ala Phe Asp Asn Leu Xaa Tyr Trp Ala Gln Asn
1               5                   10                  15

Ser Ser Glu Gln Gly
            20

(2) INFORMATION FOR SEQ ID NO:30:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: one-of(11,12)
            (D) OTHER INFORMATION: /note= "Xaa is phosphotyrosine."

(xi) SEQUENCE DESCRIPTION: SEQ ID NO:30:

Pro Ala Phe Ser Pro Ala Phe Asp Asn Leu Xaa Xaa Trp Ala Gln Asn
1               5                   10                  15

Ser Ser Glu Gln Gly
            20

(2) INFORMATION FOR SEQ ID NO:31:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: one-of(12)
            (D) OTHER INFORMATION: /note= "Xaa is phosphotyrosine."

(xi) SEQUENCE DESCRIPTION: SEQ ID NO:31:

Pro Ala Phe Ser Pro Ala Phe Asp Asn Leu Tyr Xaa Trp Asp Ala Asn
1               5                   10                  15

Ser Ser Glu Gln Gly
            20

(2) INFORMATION FOR SEQ ID NO:32:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: one-of(11)
            (D) OTHER INFORMATION: /note= "Xaa is phosphotyrosine."

(xi) SEQUENCE DESCRIPTION: SEQ ID NO:32:

Pro Ala Phe Ser Pro Ala Phe Asp Asn Leu Xaa Tyr Trp Asp Ala Asn
1               5                   10                  15

Ser Ser Glu Gln Gly
            20

(2) INFORMATION FOR SEQ ID NO:33:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:33:

Pro Ala Phe Ser Pro Ala Phe Asp Asn Leu Xaa Xaa Trp Asp Ala Asn
1               5                   10                  15

Ser Ser Glu Gln Gly
            20

(2) INFORMATION FOR SEQ ID NO:34:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:34:

Pro Ala Phe Ser Pro Ala Phe Asp Asn Leu Tyr Xaa Trp Asp Asn Asn
1               5                   10                  15

Ser Ser Glu Gln Gly
            20

(2) INFORMATION FOR SEQ ID NO:35:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:35:

Pro Ala Phe Ser Pro Ala Phe Asp Asn Leu Xaa Tyr Trp Asp Asn Asn
1               5                   10                  15

Ser Ser Glu Gln Gly
            20

(2) INFORMATION FOR SEQ ID NO:36:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:36:

Pro Ala Phe Ser Pro Ala Phe Asp Asn Leu Xaa Xaa Trp Asp Asn Asn
1               5                   10                  15

Ser Ser Glu Gln Gly
            20

(2) INFORMATION FOR SEQ ID NO:37:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:37:

Pro Ala Phe Ser Pro Ala Phe Asp Asn Leu Tyr Xaa Asp Asp Gln Asn
1               5                   10                  15

Ser Ser Glu Gln Gly
            20

(2) INFORMATION FOR SEQ ID NO:38:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:38:

Pro Ala Phe Ser Pro Ala Phe Asp Asn Leu Xaa Tyr Trp Asp Asp Asn
1               5                   10                  15

Ser Ser Glu Gln Gly
            20

(2) INFORMATION FOR SEQ ID NO:39:

(i) SEQUENCE CHARACTERISTICS:
        (A) LENGTH: 21 amino acids
        (B) TYPE: amino acid
        (C) STRANDEDNESS: single
        (D) TOPOLOGY: linear

```
    (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:39:

Pro Ala Phe Ser Pro Ala Phe Asp Asn Leu Xaa Xaa Trp Asp Asp Asn
1               5                  10                  15

Ser Ser Glu Gln Gly
            20

(2) INFORMATION FOR SEQ ID NO:40:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:40:

Pro Ala Phe Ser Pro Ala Phe Asp Asn Leu Ala Xaa Trp Asp Gln Ala
1               5                  10                  15

Ser Ser Glu Gln Gly
            20

(2) INFORMATION FOR SEQ ID NO:41:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:41:

Pro Ala Phe Ser Pro Ala Phe Asp Asn Leu Xaa Tyr Trp Asp Gln Ala
1               5                  10                  15

Ser Ser Glu Gln Gly
            20

(2) INFORMATION FOR SEQ ID NO:42:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."
```

(xi) SEQUENCE DESCRIPTION: SEQ ID NO:42:

Pro Ala Phe Ser Pro Ala Phe Asp Asn Leu Xaa Xaa Trp Asp Gln Ala
1               5                   10                  15

Ser Ser Glu Gln Gly
            20

(2) INFORMATION FOR SEQ ID NO:43:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:43:

Pro Ala Phe Ser Pro Ala Phe Asp Asn Leu Tyr Xaa Trp Asp Gln Asn
1               5                   10                  15

Ala Ser Glu Gln Gly
            20

(2) INFORMATION FOR SEQ ID NO:44:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:44:

Pro Ala Phe Ser Pro Ala Phe Asp Asn Leu Xaa Tyr Trp Asp Gln Asn
1               5                   10                  15

Ala Ser Glu Gln Gly
            20

(2) INFORMATION FOR SEQ ID NO:45:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:45:

Pro Ala Phe Ser Pro Ala Phe Asp Asn Leu Xaa Xaa Trp Asp Gln Asn
1               5                   10                  15

Ala Ser Glu Gln Gly
            20

(2) INFORMATION FOR SEQ ID NO:46:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:46:

Ala Phe Gly Gly Ala Val Glu Asn Pro Glu Xaa Leu Ala Pro Arg Ala
1               5                   10                  15

Gly Thr Ala Ser Gln
            20

(2) INFORMATION FOR SEQ ID NO:47:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:47:

Glu Gly Thr Pro Thr Ala Glu Asn Pro Glu Xaa Leu Gly Leu Asp Val
1               5                   10                  15

Pro Val (2) INFORMATION FOR SEQ ID NO:48:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

Pro Ala Phe Ser Pro Ala Phe Asp Asn Leu Tyr Tyr Trp Asp Gln Asn
1               5                   10                  15

Ser Ser Glu Gln Gly
            20

(2) INFORMATION FOR SEQ ID NO:49:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Region
    (B) LOCATION: one-of(11)
    (D) OTHER INFORMATION: /note= "Xaa is phosphotyrosine."

(xi) SEQUENCE DESCRIPTION: SEQ ID NO:49:

Ala Pro Leu Ala Cys Ser Pro Gln Pro Glu Xaa Val Asn Gln Pro Glu
1               5                   10                  15

Val Arg Pro Gln Ser
            20

(2) INFORMATION FOR SEQ ID NO:50:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:50:

Ser Pro His Asp Leu Ser Pro Leu Gln Arg Xaa Ser Glu Asp Pro Thr
1               5                   10                  15

Leu Pro Leu (2) INFORMATION FOR SEQ ID NO:51:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11)
        (D) OTHER INFORMATION: /note= "Xaa is phosphotyrosine."

(xi) SEQUENCE DESCRIPTION: SEQ ID NO:51:

Thr Leu Pro Leu Pro Pro Glu Thr Asp Gly Xaa Val Ala Pro Leu Ala
1               5                   10                  15

Cys Ser Pro Gln
            20

(2) INFORMATION FOR SEQ ID NO:52:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(4)
        (D) OTHER INFORMATION: /note= "Xaa is phosphotyrosine."

(xi) SEQUENCE DESCRIPTION: SEQ ID NO:52:

Asn Xaa Xaa Xaa
1

(2) INFORMATION FOR SEQ ID NO:53:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(7)
        (D) OTHER INFORMATION: /note= "Xaa is phosphotyrosine."

(xi) SEQUENCE DESCRIPTION: SEQ ID NO:53:

Leu Leu Ser Asn Pro Thr Xaa Ser Val Met Arg
1          5               10

(2) INFORMATION FOR SEQ ID NO:54:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(7)
        (D) OTHER INFORMATION: /note= "Xaa is phosphotyrosine."

(xi) SEQUENCE DESCRIPTION: SEQ ID NO:54:

Ala Phe Asp Asn Pro Asp Xaa Trp His Phe Arg Leu Phe
1          5               10

(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(6)
        (D) OTHER INFORMATION: /note= "Xaa is phosphotyrosine."

(xi) SEQUENCE DESCRIPTION: SEQ ID NO:55:

Ile Glu Asn Pro Gln Xaa Phe Ser Asp Ala
1          5               10

(2) INFORMATION FOR SEQ ID NO:56:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide

```
    (ix) FEATURE:
        (A) NAME/KEY: Region
        (B) LOCATION: one-of(7)
        (D) OTHER INFORMATION: /note= "Xaa is phosphotyrosine."

(xi) SEQUENCE DESCRIPTION: SEQ ID NO:56:

Ser Leu Asp Asn Pro Asp Xaa Gln Gln Asp Phe Phe
1               5                   10

(2) INFORMATION FOR SEQ ID NO:57:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(4)
        (D) OTHER INFORMATION: /note= "Xaa is phosphotyrosine."

(xi) SEQUENCE DESCRIPTION: SEQ ID NO:57:

Asn Pro Xaa Xaa
1

(2) INFORMATION FOR SEQ ID NO:58:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(4)
        (D) OTHER INFORMATION: /note= "Xaa is phosphotyrosine."

(xi) SEQUENCE DESCRIPTION: SEQ ID NO:58:

Asn Leu Xaa Xaa
1

(2) INFORMATION FOR SEQ ID NO:59:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:59:

Asp Ser Trp Asp Gln Asn Gln Leu Phe Ser Xaa Xaa Ser Phe Ala Pro
1               5                   10                  15

Glu Gly Pro Ala Asn
            20
```

(2) INFORMATION FOR SEQ ID NO:60:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(4,18)
        (D) OTHER INFORMATION: /note= "Xaa is phosphotyrosine."

(xi) SEQUENCE DESCRIPTION: SEQ ID NO:60:

```
Asp Ser Trp Xaa Ser Gln Asn Gln Leu Phe Asp Ser Phe Ala Pro Glu
1               5                   10                  15

Gly Xaa Pro Ala Asn
            20
```

(2) INFORMATION FOR SEQ ID NO:61:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:61:

```
Pro Ala Phe Ser Pro Ala Phe Asp Ala Leu Tyr Xaa Trp Asp Gln Asn
1               5                   10                  15

Ser Ser Glu Gln Gly
            20
```

(2) INFORMATION FOR SEQ ID NO:62:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:62:

```
Pro Ala Phe Ser Pro Ala Phe Asp Gln Leu Tyr Xaa Trp Asp Gln Asn
1               5                   10                  15

Ser Ser Glu Gln Gly
            20
```

(2) INFORMATION FOR SEQ ID NO:63:

(i) SEQUENCE CHARACTERISTICS:
        (A) LENGTH: 21 amino acids
        (B) TYPE: amino acid
        (C) STRANDEDNESS: single
        (D) TOPOLOGY: linear

```
        (ii) MOLECULE TYPE: peptide (ix) FEATURE:
             (A) NAME/KEY: Region
             (B) LOCATION: one-of(12)
             (D) OTHER INFORMATION: /note= "Xaa is phosphotyrosine."

(xi) SEQUENCE DESCRIPTION: SEQ ID NO:63:

Pro Ala Phe Ser Pro Ala Phe Asp Asp Leu Tyr Xaa Trp Asp Gln Asn
1               5                   10                  15

Ser Ser Glu Gln Gly
            20

(2) INFORMATION FOR SEQ ID NO:64:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: one-of(13)
             (D) OTHER INFORMATION: /note= "Xaa is phosphotyrosine."

(xi) SEQUENCE DESCRIPTION: SEQ ID NO:64:

Pro Ala Phe Ser Pro Ala Phe Asp Asn Leu Ala Tyr Xaa Trp Asp Gln
1               5                   10                  15

Asn Ser Ser Glu Gln Gly
                20

(2) INFORMATION FOR SEQ ID NO:65:

(i) SEQUENCE CHARACTERISTICS:
             (A) LENGTH: 22 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: one-of(13)
             (D) OTHER INFORMATION: /note= "Xaa is phosphotyrosine."

(xi) SEQUENCE DESCRIPTION: SEQ ID NO:65:

Pro Ala Phe Ser Pro Ala Phe Asp Asn Leu Phe Tyr Xaa Trp Asp Gln
1               5                   10                  15

Asn Ser Ser Glu Gln Gly
                20

(2) INFORMATION FOR SEQ ID NO:66:

(i) SEQUENCE CHARACTERISTICS:
             (A) LENGTH: 21 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Region
             (B) LOCATION: one-of(12)
             (D) OTHER INFORMATION: /note= "Xaa is phosphotyrosine."
```

(xi) SEQUENCE DESCRIPTION: SEQ ID NO:66:

Pro Ala Phe Ser Pro Ala Phe Asp Asp Leu Tyr Xaa Ala Asp Gln Asn
1               5                   10                  15

Ser Ser Glu Gln Gly
            20

(2) INFORMATION FOR SEQ ID NO:67:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:67:

Pro Ala Phe Ser Pro Ala Phe Asp Asn Leu Tyr Xaa Trp Asp Asn
1               5                   10                  15

Ser Ser Glu Gln Gly
            20

(2) INFORMATION FOR SEQ ID NO:68:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(12)
        (D) OTHER INFORMATION: /note= "Xaa is phosphotyrosine."

(xi) SEQUENCE DESCRIPTION: SEQ ID NO:68:

Pro Ala Phe Ser Pro Ala Phe Asp Asn Leu Tyr Xaa Trp Asp Gln Ala
1               5                   10                  15

Ser Ser Glu Gln Gly
            20

(2) INFORMATION FOR SEQ ID NO:69:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphoserine."

(xi) SEQUENCE DESCRIPTION: SEQ ID NO:69:

Pro Ala Phe Ser Pro Ala Phe Asp Asn Leu Xaa Xaa Trp Asp Gln Asn
1               5                   10                  15

Ser Ser Glu Gln Gly
            20

(2) INFORMATION FOR SEQ ID NO:70:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:70:

Pro Ala Phe Ser Pro Ala Phe Asp Asn Leu Glu Glu Trp Asp Gln Asn
1               5                   10                  15

Ser Ser Glu Gln Gly
            20

(2) INFORMATION FOR SEQ ID NO:71:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Pro Ala Phe Ser Pro Ala Phe Asp Asn Leu Phe Phe Trp Asp Gln Asn
1               5                   10                  15

Ser Ser Glu Gln Gly
            20

(2) INFORMATION FOR SEQ ID NO:72:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

(xi) SEQUENCE DESCRIPTION: SEQ ID NO:72:

Pro Ala Phe Ser Pro Ala Phe Asp Gln Leu Xaa Xaa Trp Asp Gln Asn
1               5                   10                  15

Ser Ser Glu Gln Gly
            20

(2) INFORMATION FOR SEQ ID NO:73:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(11,12)
        (D) OTHER INFORMATION: /note= "Xaa is phosphotyrosine."

-continued

```
    (xi) SEQUENCE DESCRIPTION: SEQ ID NO:73:

Pro Ala Phe Ser Pro Ala Phe Asp Asp Leu Xaa Xaa Trp Asp Gln Asn
1               5                   10                  15

Ser Ser Glu Gln Gly
            20

(2) INFORMATION FOR SEQ ID NO:74:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Region
        (B) LOCATION: one-of(5)
        (D) OTHER INFORMATION: /note= "Xaa is phosphotyrosine."

(xi) SEQUENCE DESCRIPTION: SEQ ID NO:74:

Asp Asn Leu Tyr Xaa Trp
1               5
```